United States Patent [19]

Takiguchi et al.

[11] Patent Number: 5,756,666
[45] Date of Patent: May 26, 1998

[54] PEPTIDES CAPABLE OF INDUCING IMMUNE RESPONSE TO HIV

[75] Inventors: Masafumi Takiguchi, Tokyo; Kiyoshi Miwa, Kawasaki, both of Japan

[73] Assignee: Ajinomoto Co., Inc., Tokyo, Japan

[21] Appl. No.: 615,181

[22] PCT Filed: Oct. 19, 1994

[86] PCT No.: PCT/JP94/01756

§ 371 Date: Apr. 4, 1996

§ 102(e) Date: Apr. 4, 1996

[87] PCT Pub. No.: WO95/11255

PCT Pub. Date: Apr. 27, 1995

[30] Foreign Application Priority Data

Oct. 19, 1993 [JP] Japan .................... 5-261302

[51] Int. Cl.$^6$ .......... A61K 38/04; A61K 39/21; A61K 39/00; C07K 5/00

[52] U.S. Cl. .............. 530/327; 530/328; 424/208.1; 424/204.1; 424/184.1

[58] Field of Search .............. 424/208.1, 184.1, 424/204.1; 530/327, 328

[56] References Cited

FOREIGN PATENT DOCUMENTS

WO 88/06626 9/1988 WIPO.

OTHER PUBLICATIONS

Fox, 1994, "No winners against AIDS", Biotechnology vol. 12:128.
Butini, et al, "Comparative analysis of HIV-specific CTL..." Abstract J306 J. Cell. Biochem. Suppl. 18B.
Koenig, et al, 1990, "Mapping the fine specifcity of..." J. Immunnol. 145(1):127–135.
Proc. Natl. Acd. Sci. USA. Vol. 84, pp. 1434–1438, Mar. 1987, Paul A. Luciw, et al., "Mutational Analysis of the Human Immunodeficiency Virus: The orf–B Region Down–Regulates Virus Replication".
Science, vol. 232, pp. 238–243, April 11, 1986, Phyllis J. Kanki, et al., "New Human T–Lymphotropic Retrovirus Related To Simian T–Lymphotropic Virus Type III (STLV–III$_{AGM}$)".
Proc. Natl. Acad. Sci. USA, vol. 84, pp. 6924–6928, Oct. 1987, James R. Rusche, et al., "Humoral Immune Response to the Entire Human Immunodeficiency Virus Envelope Glycoprotein Made In Insect Cells".
Annals of Internal Medicine, vol. 114, No. 2, pp. 119–127, Jan. 15, 1991, Raphael Dolin, et al., "The Safety and Immunogenicity of a Human Immunodeficiency Virus Type 1 (HIV–1) Recombinant gp160 Candidate Vaccine in Humans".
Nature, vol. 355, pp. 728–731, Feb. 20, 1992, E.A. Emini, et al., "Prevention of HIV–1 Infection in Chimpanzees By gp120 V3 Domain–Specific Monoclonal Antibody".
Nature, vol. 332, pp. 728–731, Apr. 21, 1988, Daniel Zagury, et al., "A Group Specific Anamnestic Immune Reaction Against HIV–1 Induced By a Candidate Vaccine Against AIDS".
Nature, vol. 351, pp. 479–483, Jun. 6, 1991, Anna Aldovini, et al., "Humoral and Cell–Mediated Immune Responses To Live Recombinant BCG–HIV Vaccines".
The Lancet, vol. 337, pp. 1034–1035, Apr. 27, 1991, J.C. Guillaume, et al., "Vaccinia From Recombinant Virus Expressing HIV Genes".
Proc. Natl. Acad. Sci. USA, vol. 89, pp. 2546–2550, Apr. 1992, Chang–Yuil Kang, et al., "Anti–Idiotype Monoclonal Antibody Elicits Broadly Neutralizing Anti–gp120 Antibodies In Monkeys".
Proc. Natl. Acad. Sci. USA, vol. 86, pp. 6768–6772, Sep. 1989, Kashi Javaherian, et al., "Principal Neutralizing Domain of the Human Immunodeficiency Virus Type 1 Envelope Protein".
Nature, vol. 360, pp. 434–439, Dec. 3, 1992, Adrian V.S. Hill, et al., "Molecular Analysis of the Association of HLA–B53 and Resistance to Severe Malaria".
Clinical Experiments and Microorganisms, ( Rinsho To Biseibutsu),vol. 20, No. 1, pp. 054–062, 1993, Kenji Okuda, et al.
BiOmedica, vol. 8, No. 2, pp. 41–47, 1993, Albert T. Profy.
The Journal of Infectious Diseases, vol. 164, pp. 178–182, 1991, Mario Clerici, et al., "Exposure To Human Immunodeficiency Virus Type 1–Specific T Helper Cell Responses Before Detection of Infection By Polymerase Chain Reaction and Serum Antibodies".
Proc. Natl. Acad. Sci. USA, vol. 85, pp. 3105–3109, May 1988, Hidemi Takahashi, et al., "An Immunodominant Epitope of the Human Immunodeficiency Virus Envelope Glycoprotein gp160 Recognized By Class I Major Histocompatibility Complex Molecule–Restricted Murine Cytotoxic T Lymphocytes".
Nature, vol. 351, pp. 290–297, May 23, 1991, Kirsten Falk, et al., "Allel–Specific Motifs Revealed By Sequencing of Self–Peptides Eluted From MHC Molecules".
Eur. J. Immunol., Vol. 22, pp. 2453–2456, 1992, Olaf Roetzschke, et al., "Peptide Motifs of Closely Related HLA Class I Molecules Encompass Substantial Differences".
Nature, vol. 353, pp. 326–329, Sep. 26, 1991, T.S. Jardetzky, et al., "Identification of Self Peptides Bound to Purified HLA–B27".

(List continued on next page.)

*Primary Examiner*—Lynette F. Smith
*Attorney, Agent, or Firm*—Oblon, Spivak, McClelland, Maier & Neustadt, P.C.

[57] ABSTRACT

Herein disclosed is a peptide which is a fragment of the whole protein of HIV, the fragment being a peptide having a sequence of successive 8 to 11 amino acid residues, which corresponds to an HLA-binding motif, which actually binds to HLA and which can induce killer cells capable of attacking HIV-infected cells as target cells. The peptide is effective as an anti-AIDS agent for preventing and curing AIDS.

22 Claims, 3 Drawing Sheets

OTHER PUBLICATIONS

Immunogenetics, vol. 38, pp. 161–162, 1993, Kirsten Falk, et al., "Peptide Motifs of HLA–B35 and –B37 Molecules".

Nature, vol. 313, pp. 277–283, Jan. 24, 1985, Lee Ratner, et al., "Complete Nucleotide Sequence of the AIDS Virus, HTLV–III".

Proc. Natl. Acad. Sci. USA, vol. 83, pp. 2209–2213, Apr. 1986, Suresh K. Arya, et al., "Three Novel Genes of Human T-Lymphotropic Virus Type III: Immune Reactivity of Their Products With Sera From Acquired Immune Deficiency Syndrome Patients".

The Journal of Immunology, vol. 142, No. 8, pp. 2911–2917, Apr. 15, 1989, Hans–Gustaf Ljunggren, et al., "Molecular Analysis of H–2–Deficient Lymphoma Lens".

Nature, vol. 308, pp. 457–460, Mar. 29, 1984, B. Morein, et al., "ISCOM, A Novel Structure For Antigenic Presentation of Membrane Proteins From Enveloped Viruses".

Nature, vol. 344, pp. 873–875, Apr. 26, 1990 Hidemi Takahashi, et al., "Induction of $CD8^+$ Cytotoxic T Cells By Immunization With Purified HIV–1 Envelope Protein In ISCOMs".

The Journal of Immmunology, vol. 148, No. 5, pp. 1438–1444, Mar. 1, 1992, "pH Dependence of the Interaction Between Immunogenic Peptides and MHC Class II Molecules".

The Journal of Immunology, vol. 148, No. 5, pp. 1585–1589, Mar. 1, 1992, Ramani Reddy, et al., "In Vivo Cytotoxic T Lymphocyte Induction with Soluble Proteins Administered in Liposomes".

Journal of Virology, vol. 65, No. 1, pp. 489–493, Jan. 1991, David D. Ho, et al., "Conformational Epitope On gp120 Important In CD4 Binding and Human Immunodeficiency Virus Type 1 Neutralization Identified By a Human Monoclonal Antibody".

Science, vol. 255, pp. 333–337, Jan. 17, 1992, Hidemi Takahashi, et al., Induction of Broadly Cross–Reactive Cytotoxic T Cells Recognizing an HIV–1 Envelope Determinant.

The New England Journal of Medicine, vol. 313, No. 23, pp. 1485–1492, Dec. 5, 1985, Steven A. Rosenberg, et al., "Observations of the Systemic Administration of Autologous Lymphokine–Activated Killer Cells and Recombinant Interleukin–2 To Patients With Metastatic Cancer".

Science, vol. 233, pp. 1318–1321, Sep. 19, 1986, Steven A. Rosenberg, et al., "A New Approach To the Adoptive Immunotherapy of Cancer With Tumor–Infiltrating Lymphocytes".

J. Exp. Med., vol. 178, pp. 197–209, Jul. 1993, C. Kendall Stover, et al., "Protective Immunity Elicited By Recombinant Bacille Calmette–Gurin (BCG) Expressing Outer Surface Protein A (OspA) Lipoprotein: A Candidate Lyme Disease Vaccine".

Immunogenetics, vol. 30, pp. 76–80, 1989, Takashi Ooba, et al., "The Structure of HLA–B35 Suggests that it is Derived From HLA–Bw58 By Two Genetic Mechanisms".

Proc. Natl. Acad. Sci. USA, vol. 82, pp. 8614–8618, Dec. 1985, Helene L. Coppin, et al., "HLA–B Locus Polymorphism: Studies With a Specific Hybridization Probe".

Nature, vol. 346, pp. 476–481, Aug. 2, 1990, Hans–Gustaf Ljunggren, et al., "Empty MHC Class I Molecules Come Out In the Cold".

Chugai Igaku Co., Ltd., "Novel Method of Searching of Functions of Lymphocytes", pp. 17–19, 1987, Junichi Yata, et al.

Bunshi Menekigaku (Molecular Immunology) I, No. 12, pp. 4–9, 1989, Shin–Seikagaku Jikken, "New Lectures On Biochemical Experiments".

The EMBO Journal, vol. 5, No. 5, pp. 943–949, 1986, Russel D. Salter, et al., "Impaired Assembly and Transport of HLA–A and –B Antigens In a Mutant TxB Cell Hybrid".

Experimental Medicine, vol. 11, No. 5, pp. 655–661, 1993, Hidemi Takahashi, et al., "Analysis of Cytotoxic T Lymphocytes responses to HIV: For Vaccine Development", no translation.

SEQUENCE LISTING ( 1 ) GENERAL INFORMATION:

( i i i ) NUMBER OF SEQUENCES: 115

( 2 ) INFORMATION FOR SEQ ID NO:1:

( i ) SEQUENCE CHARACTERISTICS:
   ( A ) LENGTH: 9 amino acids
   ( B ) TYPE: amino acid
   ( C ) STRANDEDNESS: single
   ( D ) TOPOLOGY: linear ( i i ) MOLECULE TYPE: peptide ( v i ) ORIGINAL SOURCE:
   ( A ) ORGANISM: HUMAN IMMUNODEFICIENCY VIRUS ( x i ) SEQUENCE DESCRIPTION: SEQ ID NO:1:

Asn Pro Asp Ile Val Ile Tyr Gln Tyr
1               5

( 2 ) INFORMATION FOR SEQ ID NO:2:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( v i ) ORIGINAL SOURCE:
      ( A ) ORGANISM: HUMAN IMMUNODEFICIENCY VIRUS ( x i ) SEQUENCE DESCRIPTION: SEQ ID NO:2:

Phe Pro Val Arg Pro Gln Val Pro Leu
1               5

( 2 ) INFORMATION FOR SEQ ID NO:3:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( v i ) ORIGINAL SOURCE:
      ( A ) ORGANISM: HUMAN IMMUNODEFICIENCY VIRUS ( x i ) SEQUENCE DESCRIPTION: SEQ ID NO:3:

Thr Pro Pro Leu Val Lys Leu Trp Tyr
1               5

( 2 ) INFORMATION FOR SEQ ID NO:4:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( v i ) ORIGINAL SOURCE:
      ( A ) ORGANISM: HUMAN IMMUNODEFICIENCY VIRUS ( x i ) SEQUENCE DESCRIPTION: SEQ ID NO:4:

Glu Pro Ile Val Gly Ala Glu Thr Phe Tyr
1               5                   10

( 2 ) INFORMATION FOR SEQ ID NO:5:

( i ) SEQUENCE CHARACTERISTICS:
      ( A ) LENGTH: 9 amino acids
      ( B ) TYPE: amino acid
      ( C ) STRANDEDNESS: single ( D ) TOPOLOGY: linear ( i i ) MOLECULE TYPE: peptide ( v i ) ORIGINAL SOURCE:
    ( A ) ORGANISM: HUMAN IMMUNODEFICIENCY VIRUS ( x i ) SEQUENCE DESCRIPTION: SEQ ID NO:5:

Ser Pro Ala Ile Phe Gln Ser Ser Met
1               5

( 2 ) INFORMATION FOR SEQ ID NO:6:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:6:

Tyr Pro Leu Thr Phe Gly Trp Cys Phe
1               5

( 2 ) INFORMATION FOR SEQ ID NO:7:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:7:

Glu Pro Ile Val Gly Ala Glu Thr Phe
1               5

( 2 ) INFORMATION FOR SEQ ID NO:8:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:8:

Val Pro Leu Asp Lys Asp Phe Arg Lys Tyr
1               5                   10

( 2 ) INFORMATION FOR SEQ ID NO:9:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
    ( A ) ORGANISM: HUMAN IMMUNODEFICIENCY VIRUS ( x i ) SEQUENCE DESCRIPTION: SEQ ID NO:9:

Arg Pro Gln Val Pro Leu Arg Pro Met Thr Tyr
1               5                   10

( 2 ) INFORMATION FOR SEQ ID NO:10:

( i ) SEQUENCE CHARACTERISTICS:
       ( A ) LENGTH: 9 amino acids
       ( B ) TYPE: amino acid
       ( C ) STRANDEDNESS: single
       ( D ) TOPOLOGY: linear ( i i ) MOLECULE TYPE: peptide ( v i ) ORIGINAL SOURCE:
       ( A ) ORGANISM: HUMAN IMMUNODEFICIENCY VIRUS ( x i ) SEQUENCE DESCRIPTION: SEQ ID NO:10:

Ile Pro Leu Thr Glu Glu Ala Glu Leu
1               5

( 2 ) INFORMATION FOR SEQ ID NO:11:

( i ) SEQUENCE CHARACTERISTICS:
       ( A ) LENGTH: 9 amino acids
       ( B ) TYPE: amino acid
       ( C ) STRANDEDNESS: single
       ( D ) TOPOLOGY: linear ( i i ) MOLECULE TYPE: peptide ( v i ) ORIGINAL SOURCE:
       ( A ) ORGANISM: HUMAN IMMUNODEFICIENCY VIRUS ( x i ) SEQUENCE DESCRIPTION: SEQ ID NO:11:

Asp Pro Asn Pro Gln Glu Val Val Leu
1               5

( 2 ) INFORMATION FOR SEQ ID NO:12:

( i ) SEQUENCE CHARACTERISTICS:
       ( A ) LENGTH: 9 amino acids
       ( B ) TYPE: amino acid
       ( C ) STRANDEDNESS: single
       ( D ) TOPOLOGY: linear ( i i ) MOLECULE TYPE: peptide ( v i ) ORIGINAL SOURCE:
       ( A ) ORGANISM: HUMAN IMMUNODEFICIENCY VIRUS ( x i ) SEQUENCE DESCRIPTION: SEQ ID NO:12:

Arg Pro Ile Val Ser Thr Gln Leu Leu
1               5

( 2 ) INFORMATION FOR SEQ ID NO:13:

( i ) SEQUENCE CHARACTERISTICS:
       ( A ) LENGTH: 9 amino acids
       ( B ) TYPE: amino acid
       ( C ) STRANDEDNESS: single
       ( D ) TOPOLOGY: linear ( i i ) MOLECULE TYPE: peptide ( v i ) ORIGINAL SOURCE:
       ( A ) ORGANISM: HUMAN IMMUNODEFICIENCY VIRUS ( x i ) SEQUENCE DESCRIPTION: SEQ ID NO:13:

```
Leu  Pro  Cys  Arg  Ile  Lys  Gln  Ile  Ile
1                   5
```

(2) INFORMATION FOR SEQ ID NO:14:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: HUMAN IMMUNODEFICIENCY VIRUS (xi) SEQUENCE DESCRIPTION: SEQ ID NO:14:

```
Phe  Pro  Gln  Ser  Arg  Thr  Glu  Pro  Thr
1                   5
```

(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: HUMAN IMMUNODEFICIENCY VIRUS (xi) SEQUENCE DESCRIPTION: SEQ ID NO:15:

```
Phe  Pro  Ile  Ser  Pro  Ile  Glu  Thr  Val
1                   5
```

(2) INFORMATION FOR SEQ ID NO:16:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: HUMAN IMMUNODEFICIENCY VIRUS (xi) SEQUENCE DESCRIPTION: SEQ ID NO:16:

```
Val  Pro  Leu  Asp  Glu  Asp  Phe  Arg  Lys  Tyr
1                   5                        10
```

(2) INFORMATION FOR SEQ ID NO:17:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: HUMAN IMMUNODEFICIENCY VIRUS (xi) SEQUENCE DESCRIPTION: SEQ ID NO:17:

```
Glu  Pro  Ile  Ile  Gly  Ala  Glu  Thr  Phe  Tyr
1                   5                        10
```

( 2 ) INFORMATION FOR SEQ ID NO:18:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:18:

His  Pro  Val  His  Ala  Gly  Pro  Ile  Thr
    1                        5

( 2 ) INFORMATION FOR SEQ ID NO:19:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:19:

Tyr  Pro  Leu  Ala  Ser  Leu  Lys  Ser  Leu
    1                        5

( 2 ) INFORMATION FOR SEQ ID NO:20:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:20:

Lys  Pro  Gln  Val  Pro  Leu  Arg  Pro  Met  Thr  Tyr
    1                        5                              10

( 2 ) INFORMATION FOR SEQ ID NO:21:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:21:

Glu  Pro  Val  His  Gly  Val  Tyr  Tyr
    1                        5

( 2 ) INFORMATION FOR SEQ ID NO:22:

( i ) SEQUENCE CHARACTERISTICS:

(A) LENGTH: 9 amino acids
(B) TYPE: amino acid
(C) STRANDEDNESS: single
(D) TOPOLOGY: linear (i i) MOLECULE TYPE: peptide (v i) ORIGINAL SOURCE:
(A) ORGANISM: HUMAN IMMUNODEFICIENCY VIRUS (x i) SEQUENCE DESCRIPTION: SEQ ID NO:22:

Asn Pro Glu Ile Val Ile Tyr Gln Tyr
1               5

(2) INFORMATION FOR SEQ ID NO:23:

(i) SEQUENCE CHARACTERISTICS:
(A) LENGTH: 9 amino acids
(B) TYPE: amino acid
(C) STRANDEDNESS: single
(D) TOPOLOGY: linear (i i) MOLECULE TYPE: peptide (v i) ORIGINAL SOURCE:
(A) ORGANISM: HUMAN IMMUNODEFICIENCY VIRUS (x i) SEQUENCE DESCRIPTION: SEQ ID NO:23:

Val Pro Ile Val Gln Asn Ile Glu Gly
1               5

(2) INFORMATION FOR SEQ ID NO:24:

(i) SEQUENCE CHARACTERISTICS:
(A) LENGTH: 9 amino acids
(B) TYPE: amino acid
(C) STRANDEDNESS: single
(D) TOPOLOGY: linear (i i) MOLECULE TYPE: peptide (v i) ORIGINAL SOURCE:
(A) ORGANISM: HUMAN IMMUNODEFICIENCY VIRUS (x i) SEQUENCE DESCRIPTION: SEQ ID NO:24:

Leu Pro Glu Lys Asp Ser Trp Thr Val
1               5

(2) INFORMATION FOR SEQ ID NO:25:

(i) SEQUENCE CHARACTERISTICS:
(A) LENGTH: 9 amino acids
(B) TYPE: amino acid
(C) STRANDEDNESS: single
(D) TOPOLOGY: linear (i i) MOLECULE TYPE: peptide (v i) ORIGINAL SOURCE:
(A) ORGANISM: HUMAN IMMUNODEFICIENCY VIRUS (x i) SEQUENCE DESCRIPTION: SEQ ID NO:25:

Asn Pro Pro Ile Pro Val Gly Glu Ile
1               5

(2) INFORMATION FOR SEQ ID NO:26:

(i) SEQUENCE CHARACTERISTICS:
(A) LENGTH: 9 amino acids
(B) TYPE: amino acid
(C) STRANDEDNESS: single
(D) TOPOLOGY: linear ( i i ) MOLECULE TYPE: peptide ( v i ) ORIGINAL SOURCE:
    ( A ) ORGANISM: HUMAN IMMUNODEFICIENCY VIRUS ( x i ) SEQUENCE DESCRIPTION: SEQ ID NO:26:

Tyr Pro Leu Ala Ser Leu Lys Ser Leu
1               5

( 2 ) INFORMATION FOR SEQ ID NO:27:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:27:

Val Pro Val Lys Leu Lys Pro Gly Met
1               5

( 2 ) INFORMATION FOR SEQ ID NO:28:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:28:

Tyr Pro Leu Thr Ser Leu Arg Ser Leu
1               5

( 2 ) INFORMATION FOR SEQ ID NO:29:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:29:

Leu Pro Pro Val Val Ala Lys Glu Ile
1               5

( 2 ) INFORMATION FOR SEQ ID NO:30:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:

( A ) ORGANISM: HUMAN IMMUNODEFICIENCY VIRUS ( x i ) SEQUENCE DESCRIPTION: SEQ ID NO:30:

Phe Pro Arg Pro Trp Leu His Ser Leu
1               5

( 2 ) INFORMATION FOR SEQ ID NO:31:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:31:

Cys Pro Lys Val Ser Phe Glu Pro Ile
1               5

( 2 ) INFORMATION FOR SEQ ID NO:32:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:32:

Asn Ala Asn Pro Asp Cys Lys Thr Ile
1               5

( 2 ) INFORMATION FOR SEQ ID NO:33:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:33:

Thr Ala Val Gln Met Ala Val Phe Ile
1               5

( 2 ) INFORMATION FOR SEQ ID NO:34:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:34:

```
Arg Ala Phe His Thr Thr Gly Arg Ile
1               5
```

( 2 ) INFORMATION FOR SEQ ID NO:35:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:35:

```
Tyr Ala Pro Pro Ile Gly Gly Gln Ile
1               5
```

( 2 ) INFORMATION FOR SEQ ID NO:36:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:36:

```
Gln Ala Arg Gln Leu Leu Ser Gly Ile
1               5
```

( 2 ) INFORMATION FOR SEQ ID NO:37:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:37:

```
Val Ala Gln Arg Ala Tyr Arg Ala Ile
1               5
```

( 2 ) INFORMATION FOR SEQ ID NO:38:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:38:

```
Arg Ala Tyr Arg Ala Ile Leu His Ile
1               5
```

( 2 ) INFORMATION FOR SEQ ID NO:39:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:39:

Val  Gly  Pro  Thr  Pro  Val  Asn  Ile  Ile
    1                        5

( 2 ) INFORMATION FOR SEQ ID NO:40:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:40:

Gln  Gly  Trp  Lys  Gly  Ser  Pro  Ala  Ile
    1                        5

( 2 ) INFORMATION FOR SEQ ID NO:41:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:41:

Val  Gly  Gly  Leu  Val  Gly  Leu  Arg  Ile
    1                        5

( 2 ) INFORMATION FOR SEQ ID NO:42:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:42:

Asp  Ala  Arg  Ala  Tyr  Asp  Thr  Glu  Val
    1                        5

( 2 ) INFORMATION FOR SEQ ID NO:43:

( i ) SEQUENCE CHARACTERISTICS:
        ( A ) LENGTH: 9 amino acids (B) TYPE: amino acid
(C) STRANDEDNESS: single
(D) TOPOLOGY: linear (ii) MOLECULE TYPE: peptide (vi) ORIGINAL SOURCE:
(A) ORGANISM: HUMAN IMMUNODEFICIENCY VIRUS (xi) SEQUENCE DESCRIPTION: SEQ ID NO:43:

Asn Ala Leu Phe Arg Asn Leu Asp Val
1               5

(2) INFORMATION FOR SEQ ID NO:44:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (vi) ORIGINAL SOURCE:
(A) ORGANISM: HUMAN IMMUNODEFICIENCY VIRUS (xi) SEQUENCE DESCRIPTION: SEQ ID NO:44:

Ile Pro Leu Gly Asp Ala Lys Leu Val
1               5

(2) INFORMATION FOR SEQ ID NO:45:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (vi) ORIGINAL SOURCE:
(A) ORGANISM: HUMAN IMMUNODEFICIENCY VIRUS (xi) SEQUENCE DESCRIPTION: SEQ ID NO:45:

Gly Pro Cys Thr Asn Val Ser Thr Val
1               5

(2) INFORMATION FOR SEQ ID NO:46:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (vi) ORIGINAL SOURCE:
(A) ORGANISM: HUMAN IMMUNODEFICIENCY VIRUS (xi) SEQUENCE DESCRIPTION: SEQ ID NO:46:

Cys Gly His Lys Ala Ile Gly Thr Val
1               5

(2) INFORMATION FOR SEQ ID NO:47:

(i) SEQUENCE CHARACTERISTICS:
(A) LENGTH: 9 amino acids
(B) TYPE: amino acid
(C) STRANDEDNESS: single
(D) TOPOLOGY: linear ( i i ) MOLECULE TYPE: peptide ( v i ) ORIGINAL SOURCE:
    ( A ) ORGANISM: HUMAN IMMUNODEFICIENCY VIRUS ( x i ) SEQUENCE DESCRIPTION: SEQ ID NO:47:

Ile Val Met His Ser Phe Asn Cys Arg
1               5

( 2 ) INFORMATION FOR SEQ ID NO:48:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:48:

Val Leu Ala Val Glu Arg Tyr Leu Arg
1               5

( 2 ) INFORMATION FOR SEQ ID NO:49:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:49:

Asn Tyr Arg Leu Ile His Cys Asn Arg
1               5

( 2 ) INFORMATION FOR SEQ ID NO:50:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:50:

Met Val His Gln Ala Ile Ser Pro Arg
1               5

( 2 ) INFORMATION FOR SEQ ID NO:51:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:51:

Ser Val Lys Lys Leu Thr Glu Asp Arg
1                 5

( 2 ) INFORMATION FOR SEQ ID NO:52:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:52:

Ser Leu Cys Leu Phe Ser Tyr Arg Arg
1                 5

( 2 ) INFORMATION FOR SEQ ID NO:53:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:53:

Cys Leu Phe Ser Tyr Arg Arg Leu Arg
1                 5

( 2 ) INFORMATION FOR SEQ ID NO:54:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:54:

Ala Val Phe Ile His Asn Phe Lys Arg
1                 5

( 2 ) INFORMATION FOR SEQ ID NO:55:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:55:

Lys Leu Ala Phe His His Met Ala Arg (2) INFORMATION FOR SEQ ID NO:56:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: HUMAN IMMUNODEFICIENCY VIRUS (xi) SEQUENCE DESCRIPTION: SEQ ID NO:56:

```
Thr Val Gln Cys Thr His Gly Ile Arg
1               5
```

(2) INFORMATION FOR SEQ ID NO:57:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: HUMAN IMMUNODEFICIENCY VIRUS (xi) SEQUENCE DESCRIPTION: SEQ ID NO:57:

```
Ile Leu Gly Tyr Arg Val Ser Pro Arg
1               5
```

(2) INFORMATION FOR SEQ ID NO:58:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: HUMAN IMMUNODEFICIENCY VIRUS (xi) SEQUENCE DESCRIPTION: SEQ ID NO:58:

```
Ile Val Trp Gln Val Asp Arg Met Arg
1               5
```

(2) INFORMATION FOR SEQ ID NO:59:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: HUMAN IMMUNODEFICIENCY VIRUS (xi) SEQUENCE DESCRIPTION: SEQ ID NO:59:

```
Pro Val Arg Pro Gln Val Pro Leu Arg
1               5
```

(2) INFORMATION FOR SEQ ID NO:60:

( i ) SEQUENCE CHARACTERISTICS:
    ( A ) LENGTH: 9 amino acids
    ( B ) TYPE: amino acid
    ( C ) STRANDEDNESS: single
    ( D ) T (C) STRANDEDNESS: double
(D) TOPOLOGY: linear (i i) MOLECULE TYPE: DNA (genomic)

(v i) ORIGINAL SOURCE:
 (A) ORGANISM: HUMAN IMMUNODEFICIENCY VIRUS (x i) SEQUENCE DESCRIPTION: SEQ ID NO:64:

ACTCCGCCGC TGGTTAAACT GTGGTAC          27

(2) INFORMATION FOR SEQ ID NO:65:

(i) SEQUENCE CHARACTERISTICS:
 (A) LENGTH: 30 base pairs
 (B) TYPE: nucleic acid
 (C) STRANDEDNESS: double
 (D) TOPOLOGY: linear (i i) MOLECULE TYPE: DNA (genomic)

(v i) ORIGINAL SOURCE:
 (A) ORGANISM: HUMAN IMMUNODEFICIENCY VIRUS (x i) SEQUENCE DESCRIPTION: SEQ ID NO:65:

GAACCGATCG TTGGTGCTGA AACTTTCTAC          30

(2) INFORMATION FOR SEQ ID NO:66:

(i) SEQUENCE CHARACTERISTICS:
 (A) LENGTH: 27 base pairs
 (B) TYPE: nucleic acid
 (C) STRANDEDNESS: double
 (D) TOPOLOGY: linear (i i) MOLECULE TYPE: DNA (genomic)

(v i) ORIGINAL SOURCE:
 (A) ORGANISM: HUMAN IMMUNODEFICIENCY VIRUS (x i) SEQUENCE DESCRIPTION: SEQ ID NO:66:

TCTCCGGCTA TCTTCCAGTC TTCTATG          27

(2) INFORMATION FOR SEQ ID NO:67:

(i) SEQUENCE CHARACTERISTICS:
 (A) LENGTH: 8 amino acids
 (B) TYPE: amino acid
 (C) STRANDEDNESS: single
 (D) TOPOLOGY: linear (i i) MOLECULE TYPE: peptide (v i) ORIGINAL SOURCE:
 (A) ORGANISM: HUMAN IMMUNODEFICIENCY VIRUS (x i) SEQUENCE DESCRIPTION: SEQ ID NO:67:

Arg Pro Gly Gly Lys Lys Lys Tyr
1               5

(2) INFORMATION FOR SEQ ID NO:68:

(i) SEQUENCE CHARACTERISTICS:
 (A) LENGTH: 8 amino acids
 (B) TYPE: amino acid
 (C) STRANDEDNESS: single
 (D) TOPOLOGY: linear (i i) MOLECULE TYPE: peptide (v i) ORIGINAL SOURCE:
 (A) ORGANISM: HUMAN IMMUNODEFICIENCY VIRUS ( x i ) SEQUENCE DESCRIPTION: SEQ ID NO:68:

Val Pro Leu Arg Pro Met Thr Tyr
1               5

( 2 ) INFORMATION FOR SEQ ID NO:69:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:69:

Thr Pro Gly Pro Gly Ile Arg Tyr
1               5

( 2 ) INFORMATION FOR SEQ ID NO:70:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:70:

Pro Pro Ile Pro Val Gly Glu Ile Tyr
1               5

( 2 ) INFORMATION FOR SEQ ID NO:71:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:71:

Gly Pro Lys Glu Pro Phe Arg Asp Tyr
1               5

( 2 ) INFORMATION FOR SEQ ID NO:72:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:72:

Gln Pro Lys Thr Ala Cys Thr Thr Cys Tyr ( 2 ) INFORMATION FOR SEQ ID NO:73:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:73:

```
Asn Pro Pro Ile Pro Val Gly Glu Ile Tyr
 1           5                      10
```

( 2 ) INFORMATION FOR SEQ ID NO:74:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:74:

```
Glu Pro Phe Arg Asp Tyr Val Asp Arg Phe Tyr
 1           5                      10
```

( 2 ) INFORMATION FOR SEQ ID NO:75:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:75:

```
Thr Pro Gly Ile Arg Tyr Gln Tyr
 1           5
```

( 2 ) INFORMATION FOR SEQ ID NO:76:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:76:

```
Thr Pro Gln Asp Leu Asn Thr Met Leu
 1           5
```

( 2 ) INFORMATION FOR SEQ ID NO:77:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: linear ( i i ) MOLECULE TYPE: peptide ( v i ) ORIGINAL SOURCE:
  ( A ) ORGANISM: HUMAN IMMUNODEFICIENCY VIRUS ( x i ) SEQUENCE DESCRIPTION: SEQ ID NO:77:

Gly Pro Ala Ala Thr Leu Glu Glu Met
1               5

( 2 ) INFORMATION FOR SEQ ID NO:78:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( v i ) ORIGINAL SOURCE:
    ( A ) ORGANISM: HUMAN IMMUNODEFICIENCY VIRUS ( x i ) SEQUENCE DESCRIPTION: SEQ ID NO:78:

Leu Pro Gly Arg Trp Lys Pro Lys Met
  1               5

( 2 ) INFORMATION FOR SEQ ID NO:79:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( v i ) ORIGINAL SOURCE:
    ( A ) ORGANISM: HUMAN IMMUNODEFICIENCY VIRUS ( x i ) SEQUENCE DESCRIPTION: SEQ ID NO:79:

Gly Pro Lys Val Lys Gln Trp Pro Leu
  1               5

( 2 ) INFORMATION FOR SEQ ID NO:80:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( v i ) ORIGINAL SOURCE:
    ( A ) ORGANISM: HUMAN IMMUNODEFICIENCY VIRUS ( x i ) SEQUENCE DESCRIPTION: SEQ ID NO:80:

Glu Pro Ile Asp Lys Glu Leu Tyr
  1               5

( 2 ) INFORMATION FOR SEQ ID NO:81:

( i ) SEQUENCE CHARACTERISTICS:
    ( A ) LENGTH: 8 amino acids
    ( B ) TYPE: amino acid ( C ) STRANDEDNESS: single
                    ( D ) TOPOLOGY: linear ( i i ) MOLECULE TYPE: peptide ( v i ) ORIGINAL SOURCE:
                    ( A ) ORGANISM: HUMAN IMMUNODEFICIENCY VIRUS ( x i ) SEQUENCE DESCRIPTION: SEQ ID NO:81:

Glu  Pro  Val  His  Glu  Val  Tyr  Tyr
    1                   5

( 2 ) INFORMATION FOR SEQ ID NO:82:

( i ) SEQUENCE CHARACTERISTICS:
                    ( A ) LENGTH: 10 amino acids
                    ( B ) TYPE: amino acid
                    ( C ) STRANDEDNESS: single
                    ( D ) TOPOLOGY: linear ( i i ) MOLECULE TYPE: peptide ( v i ) ORIGINAL SOURCE:
                    ( A ) ORGANISM: HUMAN IMMUNODEFICIENCY VIRUS ( x i ) SEQUENCE DESCRIPTION: SEQ ID NO:82:

Gln  Pro  Arg  Thr  Ala  Cys  Asn  Asn  Cys  Tyr
    1                   5                        10

( 2 ) INFORMATION FOR SEQ ID NO:83:

( i ) SEQUENCE CHARACTERISTICS:
                    ( A ) LENGTH: 10 amino acids
                    ( B ) TYPE: amino acid
                    ( C ) STRANDEDNESS: single
                    ( D ) TOPOLOGY: linear ( i i ) MOLECULE TYPE: peptide ( v i ) ORIGINAL SOURCE:
                    ( A ) ORGANISM: HUMAN IMMUNODEFICIENCY VIRUS ( x i ) SEQUENCE DESCRIPTION: SEQ ID NO:83:

Arg  Pro  Trp  Leu  His  Ser  Leu  Gly  Gln  Tyr
    1                   5                        10

( 2 ) INFORMATION FOR SEQ ID NO:84:

( i ) SEQUENCE CHARACTERISTICS:
                    ( A ) LENGTH: 11 amino acids
                    ( B ) TYPE: amino acid
                    ( C ) STRANDEDNESS: single
                    ( D ) TOPOLOGY: linear ( i i ) MOLECULE TYPE: peptide ( v i ) ORIGINAL SOURCE:
                    ( A ) ORGANISM: HUMAN IMMUNODEFICIENCY VIRUS ( x i ) SEQUENCE DESCRIPTION: SEQ ID NO:84:

Arg  Pro  Asn  Asn  Asn  Thr  Arg  Lys  Ser  Ile  Tyr
    1                   5                        10

( 2 ) INFORMATION FOR SEQ ID NO:85:

( i ) SEQUENCE CHARACTERISTICS:
                    ( A ) LENGTH: 8 amino acids
                    ( B ) TYPE: amino acid
                    ( C ) STRANDEDNESS: single
                    ( D ) TOPOLOGY: linear ( i i ) MOLECULE TYPE: peptide ( v i ) ORIGINAL SOURCE:
   ( A ) ORGANISM: HUMAN IMMUNODEFICIENCY VIRUS ( x i ) SEQUENCE DESCRIPTION: SEQ ID NO:85:

Pro Pro Phe Leu Trp Met Gly Tyr
1               5

( 2 ) INFORMATION FOR SEQ ID NO:86:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i i ) MOLECULE TYPE: peptide ( v i ) ORIGINAL SOURCE:
      ( A ) ORGANISM: HUMAN IMMUNODEFICIENCY VIRUS ( x i ) SEQUENCE DESCRIPTION: SEQ ID NO:86:

Pro Pro Leu Val Lys Leu Trp Tyr
1               5

( 2 ) INFORMATION FOR SEQ ID NO:87:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( v i ) ORIGINAL SOURCE:
      ( A ) ORGANISM: HUMAN IMMUNODEFICIENCY VIRUS ( x i ) SEQUENCE DESCRIPTION: SEQ ID NO:87:

Glu Pro Pro Phe Leu Trp Met Gly Tyr
1               5

( 2 ) INFORMATION FOR SEQ ID NO:88:

( i ) SEQUENCE CHARACTERISTICS:
      ( A ) LENGTH: 11 amino acids
      ( B ) TYPE: amino acid
      ( C ) STRANDEDNESS: single
      ( D ) TOPOLOGY: linear ( i i ) MOLECULE TYPE: peptide ( v i ) ORIGINAL SOURCE:
      ( A ) ORGANISM: HUMAN IMMUNODEFICIENCY VIRUS ( x i ) SEQUENCE DESCRIPTION: SEQ ID NO:88:

Glu Pro Phe Lys Asn Leu Lys Thr Gly Lys Tyr
1               5                   10

( 2 ) INFORMATION FOR SEQ ID NO:89:

( i ) SEQUENCE CHARACTERISTICS:
      ( A ) LENGTH: 11 amino acids
      ( B ) TYPE: amino acid
      ( C ) STRANDEDNESS: single
      ( D ) TOPOLOGY: linear ( i i ) MOLECULE TYPE: peptide ( v i ) ORIGINAL SOURCE:
      ( A ) ORGANISM: HUMAN IMMUNODEFICIENCY VIRUS ( x i ) SEQUENCE DESCRIPTION: SEQ ID NO:89:

Ile Pro Ala Glu Thr Gly Gln Glu Thr Ala Tyr
1               5                   10

( 2 ) INFORMATION FOR SEQ ID NO:90:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( v i ) ORIGINAL SOURCE:
      ( A ) ORGANISM: HUMAN IMMUNODEFICIENCY VIRUS ( x i ) SEQUENCE DESCRIPTION: SEQ ID NO:90:

Gly Pro Gly His Lys Ala Arg Val Leu
1               5

( 2 ) INFORMATION FOR SEQ ID NO:91:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( v i ) ORIGINAL SOURCE:
      ( A ) ORGANISM: HUMAN IMMUNODEFICIENCY VIRUS ( x i ) SEQUENCE DESCRIPTION: SEQ ID NO:91:

Ala Pro Pro Glu Glu Ser Phe Arg Phe
1               5

( 2 ) INFORMATION FOR SEQ ID NO:92:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( v i ) ORIGINAL SOURCE:
      ( A ) ORGANISM: HUMAN IMMUNODEFICIENCY VIRUS ( x i ) SEQUENCE DESCRIPTION: SEQ ID NO:92:

Tyr Pro Gly Ile Lys Val Arg Gln Leu
1               5

( 2 ) INFORMATION FOR SEQ ID NO:93:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( v i ) ORIGINAL SOURCE:
      ( A ) ORGANISM: HUMAN IMMUNODEFICIENCY VIRUS ( x i ) SEQUENCE DESCRIPTION: SEQ ID NO:93:

Gln Pro Asp Lys Ser Glu Ser Glu Leu
1               5

( 2 ) INFORMATION FOR SEQ ID NO:94:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:94:

```
Val Pro Arg Arg Lys Ala Lys Ile Ile
 1               5
```

( 2 ) INFORMATION FOR SEQ ID NO:95:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:95:

```
Asp Pro Gly Leu Ala Asp Gln Leu Ile
 1               5
```

( 2 ) INFORMATION FOR SEQ ID NO:96:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:96:

```
Thr Pro Lys Lys Thr Lys Pro Pro Leu
 1               5
```

( 2 ) INFORMATION FOR SEQ ID NO:97:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:97:

```
Pro Pro Leu Pro Ser Val Lys Lys Leu
 1               5
```

( 2 ) INFORMATION FOR SEQ ID NO:98:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( v i ) ORIGINAL SOURCE:
    ( A ) ORGANISM: HUMAN IMMUNODEFICIENCY VIRUS ( x i ) SEQUENCE DESCRIPTION: SEQ ID NO:98:

Arg Pro Gln Val Pro Leu Arg Pro Met
1               5

( 2 ) INFORMATION FOR SEQ ID NO:99:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:99:

Arg Arg Pro Met Thr Tyr Lys Ala Ala Leu
1               5                   10

( 2 ) INFORMATION FOR SEQ ID NO:100:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:100:

Leu Pro Pro Leu Glu Arg Leu Thr Leu
1               5

( 2 ) INFORMATION FOR SEQ ID NO:101:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:101:

Thr Pro Ser Gln Lys Gln Glu Pro Ile
1               5

( 2 ) INFORMATION FOR SEQ ID NO:102:

( i ) SEQUENCE CHARACTERISTICS:
        ( A ) LENGTH: 9 amino acids
        ( B ) TYPE: amino acid
        ( C ) STRANDEDNESS: single ( D ) TOPOLOGY: linear ( i i ) MOLECULE TYPE: peptide ( v i ) ORIGINAL SOURCE:
   ( A ) ORGANISM: HUMAN IMMUNODEFICIENCY VIRUS ( x i ) SEQUENCE DESCRIPTION: SEQ ID NO:102:

```
Leu Pro Gly Lys Trp Lys Pro Lys Met
1               5
```

( 2 ) INFORMATION FOR SEQ ID NO:103:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( v i ) ORIGINAL SOURCE:
    ( A ) ORGANISM: HUMAN IMMUNODEFICIENCY VIRUS ( x i ) SEQUENCE DESCRIPTION: SEQ ID NO:103:

```
Lys Pro Cys Val Lys Leu Thr Pro Leu
1               5
```

( 2 ) INFORMATION FOR SEQ ID NO:104:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( v i ) ORIGINAL SOURCE:
    ( A ) ORGANISM: HUMAN IMMUNODEFICIENCY VIRUS ( x i ) SEQUENCE DESCRIPTION: SEQ ID NO:104:

```
Asp Pro Glu Ile Val Met His Ser Phe
1               5
```

( 2 ) INFORMATION FOR SEQ ID NO:105:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( v i ) ORIGINAL SOURCE:
    ( A ) ORGANISM: HUMAN IMMUNODEFICIENCY VIRUS ( x i ) SEQUENCE DESCRIPTION: SEQ ID NO:105:

```
Ser Pro Leu Ser Phe Gln Thr Arg Leu
1               5
```

( 2 ) INFORMATION FOR SEQ ID NO:106:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( v i ) ORIGINAL SOURCE:
( A ) ORGANISM: HUMAN IMMUNODEFICIENCY VIRUS ( x i ) SEQUENCE DESCRIPTION: SEQ ID NO:106:

Tyr Pro Cys Thr Val Asn Phe Thr Ile
1               5

( 2 ) INFORMATION FOR SEQ ID NO:107:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( v i ) ORIGINAL SOURCE:
( A ) ORGANISM: HUMAN IMMUNODEFICIENCY VIRUS ( x i ) SEQUENCE DESCRIPTION: SEQ ID NO:107:

Leu Pro Ala Leu Ser Thr Gly Leu Ile
1               5

( 2 ) INFORMATION FOR SEQ ID NO:108:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( v i ) ORIGINAL SOURCE:
( A ) ORGANISM: HUMAN IMMUNODEFICIENCY VIRUS ( x i ) SEQUENCE DESCRIPTION: SEQ ID NO:108:

Cys Pro Ser Gly His Ala Val Gly Ile
1               5

( 2 ) INFORMATION FOR SEQ ID NO:109:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( v i ) ORIGINAL SOURCE:
( A ) ORGANISM: HUMAN IMMUNODEFICIENCY VIRUS ( x i ) SEQUENCE DESCRIPTION: SEQ ID NO:109:

Ile Pro Thr Ser Gly Asp Val Val Ile
1               5

( 2 ) INFORMATION FOR SEQ ID NO:110:

( i ) SEQUENCE CHARACTERISTICS:
( A ) LENGTH: 9 amino acids
( B ) TYPE: amino acid
( C ) STRANDEDNESS: single
( D ) TOPOLOGY: linear ( i i ) MOLECULE TYPE: peptide ( v i ) ORIGINAL SOURCE:
( A ) ORGANISM: HUMAN IMMUNODEFICIENCY VIRUS ( x i ) SEQUENCE DESCRIPTION: SEQ ID NO:110:

```
Leu Pro Pro Thr Ile Gly Pro Pro Ile
1               5
```

( 2 ) INFORMATION FOR SEQ ID NO:111:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:111:

```
Ala Pro Thr Leu Trp Ala Arg Met Ile
1               5
```

( 2 ) INFORMATION FOR SEQ ID NO:112:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:112:

```
Glu Pro Leu Asp Leu Pro Gln Ile Ile
1               5
```

( 2 ) INFORMATION FOR SEQ ID NO:113:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:113:

```
Leu Pro Gly Pro Lys Phe Leu Gln Tyr
1               5
```

( 2 ) INFORMATION FOR SEQ ID NO:114:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: HUMAN IMMUNODEFICIENCY VIRUS ( x i ) SEQUENCE DESCRIPTION: SEQ ID NO:114:

```
Leu Pro Phe Asp Phe Thr Pro Gly Tyr
1               5
```

(2) INFORMATION FOR SEQ ID NO:115:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: HUMAN IMMUNODEFICIENCY VIRUS (xi) SEQUENCE DESCRIPTION: SEQ ID NO:115:

```
Lys Gly Ile Leu Gly Lys Val Phe Thr Leu Thr Val
 1           5                   10
```

PEPTIDES CAPABLE OF INDUCING IMMUNE RESPONSE TO HIV

BACKGROUND OF THE INVENTION

The present invention relates to peptides each having an amino acid sequence in a partial domain of a protein originated from human immunodeficiency virus (hereinafter referred to as "HIV") and capable of inducing an immune response to HIV and anti-AIDS agents comprising the peptides for preventing and curing AIDS.

It is well-known that acquired immunodeficiency disease syndrome (hereinafter referred to as "AIDS") is a disorder developed by infection with HIV. There have actively been conducted studies for developing medicines for curing the disorder and medicines such as azidothymidine (hereinafter referred to as "AZT") and dideoxyinosine (hereinafter referred to as "DDI") have already been put to practical use. However, these medicines suffer from various problems concerning, for instance, their efficacy and side-effects and accordingly, there has not yet been developed any medicine capable of completely curing the disorder and there has not yet been any prospect for the development of such medicines. On the other hand, as means for preventing infection with HIV and for inhibiting the outbreak of AIDS, vaccines capable of enhancing the immunological competence against HIV infections has been expected to be the last resort which permits the inhibition of the rapid global spread of this disorder and there have been conducted various studies for developing such vaccines. Up to date, various types of such vaccines have been planned and some of them have already been put to clinical trials. However, there has not yet been reported any vaccine which is actually proved to be effective for preventing HIV infections or for inhibiting the crisis of AIDS in human beings.

The following vaccines have conventionally been proposed:

i) A vaccine comprising inactivated or attenuated virus particles: Vaccines of this type may be developed by a method for inducing deletion, through mutation, in a gene which may be involved in the pathogenicity of HIV (Proc. Natl. Acad. Sci. USA, 1987, 84, p. 1434) and an approach which makes use of analogous viruses originated from, for instance, monkeys having an antigenicity common to HIV (Science, 1986, 232, p. 238), but these vaccines cannot be put to practical use with ease because of their potential dangerous factors.

ii) A subunit vaccine comprising a part of the antigenic protein of a virus: Vaccines of this kind may be developed by an approach which makes use of only a part of the antigenic protein among the viral particles produced using a genetic recombination technique, as an immunogen (Proc. Natl. Acad. Sci. USA, 1987, 84, p. 6924; Ann. Int. Med., 1991, 114, p. 119; Nature, 1992, 355, p. 728). This approach has most widely been used and many such vaccines have been put to clinical trials. However, the vaccine of this type suffers from various problems, to be solved, in that it does not have a sufficient neutralizing antibody titer and that it is insufficient in the durability of the antibody titer. Although this approach may be considered to be effective for enhancing the humoral immunity such as the antibody production, it can hardly bring about the activation of the cellular immunity capable of killing infectious cells. The effect of this approach alone on the prevention of infection with HIV cannot necessarily be expected while taking into consideration the mode of infection with HIV.

iii) A recombinant live vaccine derived from, for instance, vaccinia viruses and BCG bacteria: Vaccines of this type can be prepared by integrating a part of an HIV-derived gene sequence into a gene derived from vaccinia viruses (Nature, 1988, 332, p. 728) or BCG bacteria (Nature, 1991, 351, p. 479) which can proliferate in human cells, followed by expressing the recombinant gene. The vaccine of this type would theoretically be expected to exhibit a cellular immunity-enhancing effect. However, these vaccines suffer from such problems that patients whose immunological competence has lowered may seriously be infected even with, for instance, vaccinia viruses which are generally harmless (Lancet, 1991, 337, p. 1034) and that at least the vaccinia-derived recombinant live vaccines which have conventionally been proposed cannot induce any satisfactory immune response.

iv) An anti-idiotype antibody: As an example, there has been reported a method in which an anti-idiotype antibody is used as an immunogen in place of a virus antigen (Proc. Natl. Acad. Sci. USA, 1992, 89, p. 2546).

v) A synthetic peptide vaccine: As examples thereof, there have been investigated those comprising chemically synthesized peptide sequences in determinant domains of neutralizing antibodies. In particular, the V3 domain in the glycoprotein gp120 in an envelope is an essential neutralization-determining domain and therefore, attempts have been done, in which a synthetic peptide in the V3 domain is used in vaccines (Proc. Natl. Acad. Sci. USA, 1989, 86, p. 6768).

The current status of studies and developments of these vaccines are detailed in, for instance, Hidemi TAKAHASHI, JIKKEN IGAKU (Experimental Medicine), 1993, Vol. 11, pp. 655–8661; Kenji OKUDA & Tadashi YAMAKAWA, RINSHO TO BISEIBUTSU (Clinical Experiments and Microorganisms), Vol. 20, pp. 55–62; A. T. Profy, BiOmedica, Vol. 8, pp. 133–139.

The aforementioned conventional studies for developing vaccines essentially relate to humoral immunity-enhancing type vaccines which can induce neutralizing antibodies. However, since HIV's spread more easily by cell fusion of infected cells with non-infected cells rather than by infection of free virus particles, it is considered that the cellular immunity due to the cytotoxic T cell (hereinafter referred to as "CTL") capable of damaging infected cells is more important for prophylaxis than the humoral immunity caused by the neutralizing antibodies. In fact, after having examined the objects that had been exposed to a danger of HIV infection, but were not infected therewith, it has been reported that the objects possessed CTL's with considerable frequency though no blood antibody was found in them and therefore, the CTL inducement at an early stage is important for the protection from HIV infection (J. Infec. Dis., 1991, 164, p. 178).

Under such circumstances, the inventors of this invention have aimed at searching for peptides which can induce CTL capable of specifically damaging HIV-infected cells and the use of such peptides as anti-AIDS agents for preventing and curing AIDS.

In order to effectively induce CTL's which are active against HIV-infected cells, it is extremely important to identify the antigenic epitope which are recognized by CTL's and to use it in vaccines. Up to now, there has been adopted a method which comprises first of all establishing CTL clones specific to HIV and then identifying the antigenic epitope recognized by the CTL clones (Proc. Natl.

Acad. Sci. USA, 1988, 85, p. 3105). It has been believed that this method requires the synthesis of vast numbers of peptides in order to identify the HIV-antigenic epitope presented to CTL's by the class I antigen of a number of human leucocyte antigens (hereinafter referred to as "HLA's") and that the production thereof accordingly requires much time and great deal of expenses. For this reason, the identification of such epitopes has not been advanced.

CTL recognizes the epitope peptide antigenically presented by the class I antigen of the major histocompatibility antigen complex (hereinafter referred to as "MHC") which is expressed on the target cell cortex and attacks the recognized target cell. Recently, it has been proved that the epitope peptide which undergoes antigenic presentation through binding to a specific MHC class I antigen is a peptide having a length corresponding to about 9 chains and that the amino acid sequence thereof exhibits a certain regularity (motif) (Nature, 1991, 351, p. 290; Eur. J. Immunol., 1992, 22, p. 2453; Nature, 1991, 353, p. 326; Nature, 1992, 360, p. 434; Immunogenetics, 1993, 38, p. 161).

DISCLOSURE OF THE INVENTION

An object of the present invention is to provide a peptide capable of inducing an immune response to HIV.

It is another object of the present invention to provide a DNA coding for the foregoing peptide.

It is a further object of the present invention to provide an anti-AIDS agent for preventing and curing AIDS comprising the foregoing peptide.

It is a still further object of the present invention to provide a method for preparing the peptide capable of inducing an immune response to HIV.

The foregoing and other objects of the present invention will become more apparent from the description given below.

The present invention has been completed, on the basis of such finding that useful as anti-AIDS agents for preventing and curing AIDS are those prepared by a process comprising the steps of presuming HIV peptides which may bind to HLA class I antigens, on the basis of the motifs of the autoantigenic peptides capable of binding to the HLA class I antigens; synthesizing the presumed HIV peptides, selecting HIV peptides that can actually bind to the HLA class I antigens expressed, in a large quantity, on transformed cells which express a large quantity of an HLA class I antigen free of peptide bound thereto and then screening the synthesized and selected peptides bound to the HLA class I antigen and capable of stimulating the peripheral blood lymphocytes of a patient infected with HIV to thus induce CTL therein.

More specifically, the present invention provides peptides which are fragments of the whole protein of HIV, each of the fragments being a peptide having a successive sequence consisting of 8 to 11 amino acid residues, which correspond to HLA-binding motifs, which actually bind to HLA and which can induce killer cells capable of attacking HIV-infected cells as targets.

The present invention also provides DNA's coding for the foregoing peptides.

The present invention further provides anti-AIDS agents for preventing and curing AIDS, each comprising the foregoing peptide and a pharmaceutically acceptable carrier and/or a pharmaceutically acceptable diluent.

The present invention also provides a method for obtaining a peptide capable of inducing killer cells which attack HIV-infected cells as targets, the method comprising the steps of synthesizing a peptide which is a fragment of the whole protein of HIV, has a successive sequence having 8 to 11 amino acid residues and corresponds to an HLA-binding motif; selecting peptides which actually bind to HLA among these synthesized peptides; and screening peptides which can bind to HLA class I antigens to stimulate the peripheral blood lymphocytes of a patient infected with HIV and to thus induce the killer cells.

BRIEF DESCRIPTION OF THE DRAWINGS

FIG. 1 shows the results of the variation in the expression level of the antigen on the cells observed when adding autoantigenic peptide 28H (LPGPKFLQY (SEQ ID NO: 113) represented by Δ) or 37 F (LPFDFTPGY (SEQ ID NO: 114) represented by ○) having an HLA-B * 3501 antigen-binding ability or peptide MP-1 (KGILGKVFTLTV (SEQ ID NO: 115) represented by □) free of the ability to bind to the same antigen.

BEST MODE FOR CARRYING OUT THE INVENTION

Figure 1:
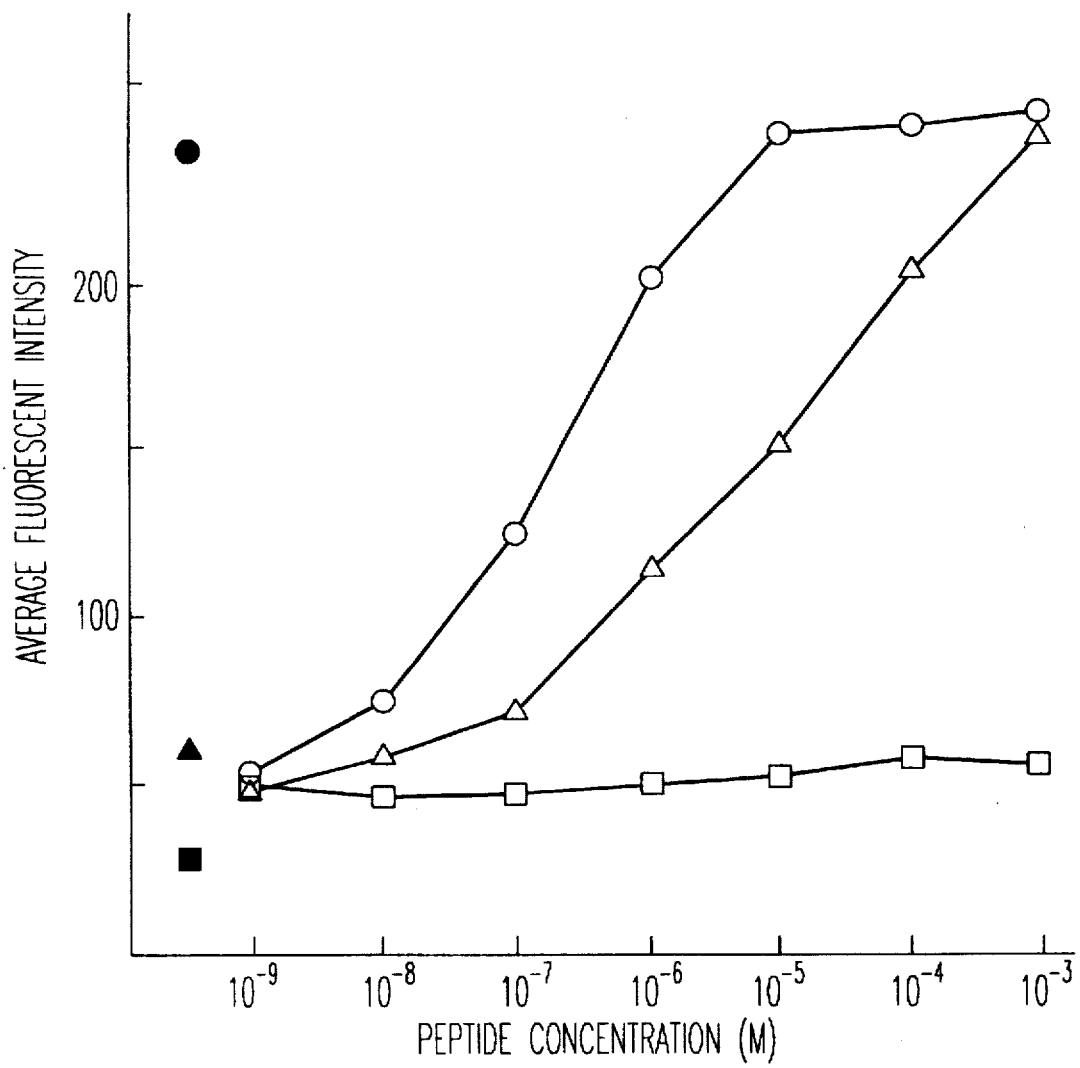
FIG. 1 shows the variation in the expression level of the HLA-B * 3501 antigen on RMA-S-B * 3501 cells. More specifically.

The whole protein of HIV is disclosed in, for instance, Nature, 1985, 313, pp. 277–283 and Proc. Natl. Acad. Sci. USA, 1986, 83, pp. 2209–2213. The peptides of the invention are fragments of the whole protein of HIV and each fragment is a peptide having a sequence consisting of successive 8 to 11, preferably 9 to 11 amino acid residues. Each peptide of the invention further corresponds to an HLA-binding motif and should practically bind to HLA. As the HLA-binding motifs, there may be listed sequences each having 8 to 11 amino acid residues, whose secondary amino acid residue is Pro and C-terminal is an amino acid residue selected from the group consisting of Tyr, Leu, Ile, Met, Phe and Ala; whose secondary amino acid residue is one selected from the group consisting of Pro, Ala and Gly and C-terminal is an amino acid residue selected from the group consisting of Ile, Leu, Val, Phe and Met; and whose secondary amino acid residue is one selected from the group consisting of Leu, Val, Tyr and Phe and C-terminal is an amino acid residue, Arg. In the present invention, whether the peptide corresponding to each HLA-binding motif can bind to HLA or not may be confirmed using cells carrying HLA class I antigens. Examples of such cells are RMA-S-B * 3501 cells, RMA-S-B * 5101 cells and RMA-S-A * 3101 cells and these cells can easily be obtained by introducing a gene such as HLA-B * 3501 gene, HLA-B * 5101 gene or HLA-A * 3101 gene into RMA-S cells. In this connection, the RMA-S cells are disclosed in Ljunggren et al., J. Immunol., 1989, 142, p. 2911.

In the present invention, each synthetic HIV peptide must further satisfy such a requirement that the peptide is capable of binding to the HLA class I antigen can actually stimulate a patient's peripheral blood lymphocytes and can thus induce CTL, i.e., can induce killer cells which can attack HIV-infected cells as targets.

As such peptides, there may be listed, for instance, those specified in Sequence Numbers 1 to 63.

The peptides each having an amino acid sequence set forth in any one of Sequence Numbers 1 to 24 are those capable of binding to the HLA-B3501 antigens and selected using the RMA-S-B * 3501 cells. The peptides each having an amino acid sequence set forth in any one of Sequence Numbers 25 to 46 are those capable of binding to the HLA-B51 antigens and selected using the RMA-S-B * 5101 cells. The peptides each having an amino acid sequence set forth in any one of Sequence Numbers 47 to 63 are those capable of binding to the HLA-A3101 antigens and selected using the RMA-S-A * 3101 cells. The means for preparing the peptides of the invention will be detailed in Examples given later.

The peptides each having an amino acid sequence set forth in any one of Sequence Numbers 1 to 63 can be synthesized or prepared by the methods known to those skilled in the art. Recent development of peptide synthesizers permits easy preparation of peptides each having several tens of residues. Alternatively, these peptides may also be prepared by connecting the DNA coding for any one of peptides having amino acid sequences set forth in Sequence Numbers 1 to 63, respectively to an appropriate expression vector and cultivating cells such as bacteria belonging to the genus Escherichia transformed by the expression vector. Such methods for preparing proteins and peptides while making use of the genetic recombination technique have been well-known to those skilled in the art.

A DNA coding for a peptide having an amino acid sequence set forth in any one of Sequence Numbers 1 to 63 can be deduced from the amino acid sequence. In addition, the codon corresponding to each amino acid residue is also well-known to those skilled in the art. When the DNA is introduced into cells to express the DNA therein, preferred codons vary from cell to cell and therefore, the codons for each DNA should be selected while taking this fact into consideration. When using, for instance, codons to which the bacterial cells belonging to the genus Escherichia give prefer, there may be listed a DNA having a base sequence set forth in Sequence Number 64 as an example of the DNA coding for a peptide having an amino acid sequence set forth in Sequence Number 3. As an example of the DNA coding for a peptide having an amino acid sequence set forth in Sequence Number 4, there may be listed a DNA having a base sequence set forth in Sequence Number 65. As an example of the DNA coding for a peptide having an amino acid sequence set forth in Sequence Number 5, there may be listed a DNA having a base sequence as set forth in Sequence Number 66.

The peptide having an amino acid sequence set forth in any one of Sequence Numbers 1 to 63 can serve as a T-cell epitope and thus induce HIV-specific CTL, and is accordingly quite useful as a vaccine. When the peptide is actually used as a vaccine, it may be administered to a patient in the form of a peptide solution per se or a combination of a peptide with an appropriate auxiliary agent using an injector. Alternatively, a good result can likewise be obtained when the peptide is percutaneously administered through mucous membrane by, for instance, spraying the solution. The unit dose of the peptide ranges from 0.1 to 100 mg, which may be administered, one timne or repeatedly, to a patient. Moreover, it is often more effective to simultaneously administer a plurality of selected epitope peptides by the foregoing administering method. The preparation of pharmaceuticals does not require the use of any particular means. As such means, there may be used, for instance, lyophilization or granulation along with a vehicle such as sugar. When the pharmaceuticals are administered by injection, they are dissolved in distilled water for injection prior to the injection. These agents are peptide compounds and therefore, they do not have any serious acute toxicity which may cause troubles in the foregoing administration methods.

Examples of auxiliary agents which can be added to vaccines to enhance the immunogenicity thereof are bacterial cell components such as BCG bacterial cells, ISCOM (Immunostimulating complex) which is extracted from the tree bark called QuillA and developed by Morein et al. (Nature, 1984, 308, p. 457; Nature, 1990, 344, p. 873), QS-21 as a saponin type auxiliary agent (J. Immunol., 1992, 148, p. 1438), liposome (J. Immunol., 1992, 148, p. 1585), aluminum hydroxide (alum) and KLH (Keyhole Limpet Hemocyanin) (J. Virol., 1991, 65, p. 489). The fact that the foregoing methods permits the inducement of an immune response such as CTL in the living body is also detailed in the aforementioned prior arts and Science, 1992, 255, p. 333.

The epitope peptides developed and identified by the present invention can effectively be used both in a method for efficiently inducing CTL in a patient's body which comprises treating, in vitro, cells collected from the patient or cells having an HLA class I antigen of the same haplotype with the corresponding epitope peptide to thus cause antigen presentation and thereafter, injecting the cells into the blood vessel of the patient and in a method which comprises adding the same peptide to peripheral blood lymphocytes originated from a patient, cultivating the cells in vitro to thus induce CTL in vitro and proliferate the cells and then putting the cultivated cells back into the patient's body. Accordingly, it is also possible to use, as an anti-AIDS vaccine, the cytotoxic T cells obtained by cultivating the peripheral blood lymphocytes carrying an HLA-B * 3501 antigen in the presence of a peptide having an amino acid sequence set forth in any one of Sequence Numbers 1 to 24. In practice, 0.01 to 1 mg of the peptide is added to $10^7$ to $10^9$ peripheral blood lymphocytes originated from a patient, then the cells are cultivated for several hours to one day and thereafter they are intravenously administered to the patient; or alternatively, the cells are continuously cultivated, in vitro, in a culture medium to which 50 U/ml of a recombinant interleukin 2 (recombinant IL-2) and 1 μg/ml of the peptide over several weeks while exchanging the culture medium at desired intervals to thus induce CTL and then intravenously injected into the patient. The culture method herein used may be those currently used and well-known to those skilled in the art. After the cultivation, the culture medium is washed by, for instance, centrifugation, suspended in, for instance, physiological saline and then administered to a patient. Such therapeutic methods which make use of cell-injection have already been adopted as a method for treating cancer and have been well-known to those skilled in the art (New Eng. J. Med., 1985, 313, p. 1485; Science, 1986, 233, p. 1318).

The CTL epitope developed and identified by the present invention can likewise effectively be used in recombinant live vaccines comprising vaccinia viruses and BCG bacteria. More specifically, if a DNA coding for a peptide having an amino acid sequence set forth in any one of Sequence Numbers 1 to 63 is incorporated into the gene coding for a recombinant antigen protein to be expressed in these recombinant live vaccines, the peptide sequence is expressed as a part of the antigenic protein and then presented by an HLA class I antigen through processing thereof within the cells to thus induce CTL which can recognize it. The method for expressing foreign genes in BCG bacterial cells is detailed in International Patent Laid-Open No. WO88/06626. The recombinant live vaccines derived from BCG bacteria are detailed in J. Exp. Med., 1993, 178, p. 197. The dose and the administration method may be determined or selected in conformity to those for the usual vaccination and BCG vaccines. The acute toxicity thereof is also in conformity with that for the vaccination and BCG vaccines currently used, provided that in case of live vaccines derived from vaccinia viruses, a patient in which the symptoms of AIDS appear and whose immunological competence is reduced may cause serious infection therewith and therefore, special care should be taken when these vaccines are used for therapeutic purposes. There has not yet been reported any such precedent for the BCG vaccines. The fact that an immune response such as CTL can be induced within the living body by such a method explained above is disclosed in, for instance, Nature, 1988, 332, p. 728 and Nature, 1991, 351, p. 479.

The HIV vaccines suffer from a serious problem in that HIV easily undergoes mutation to thus make the host immunity ineffective. For this reason, it would be highly probable that vaccines each containing only one epitope as an immunogen soon lose their efficacy. Contrary to this, the vaccines containing a large number of epitopes as immunogens, which have been developed and identified by the present invention, have extremely high usefulness.

The present invention will hereinafter be explained with reference to the following Examples.

EXAMPLE 1

(1) Presumption of HIV Peptides Capable of Binding to HLA-B * 3501 on the Basis of the Motif of HLA-B * 3501-Bondable Autoantigenic Peptide:

The motif of HLA-B * 3501-bondable autoantigenic peptide has already been revealed (Nature, 1992, 360, p. 434; Immunogenetics, 1993, 38, p. 161). It has been presumed, from the results, that peptides which are apt to bind to HLA-B * 3501 are those having 8 to 12 amino acid residues like the autoantigenic peptides, whose secondary amino acid residue is Pro and whose C-terminal posesses an amino acid residue selected from Tyr, Leu, Ile, Met and Phe, among the peptides originated from the HIV proteins. The amino acid sequences of all of the proteins constituting HIV have already been reported and therefore, those having motifs in conformity with that of the HLA-B * 3501-bondable autoantigenic peptide were selected. Fifty-eight peptides, shown in Table 1, out of the protein sequences of ARV-2 strain HIV were in agreement with the same. These peptides were synthesized using a peptide synthesizer available from Shimadzu Corp. and then used in the test for evaluating their ability to bind to the HLA-B * 3501 antigen.

TABLE 1

| | | | |
|---|---|---|---|
| HIV(B35)-1 (SEQ ID NO: 67) | RPGGKKKY | HIV(B35)-11 (SEQ ID NO: 85) | PPFLWMGY |
| HIV(B35)-1 (SEQ ID NO: 68) | VPLRPMTY | HIV(B35)-13 (SEQ ID NO: 86) | PPLVKLWY |
| HIV(B35)-3 (SEQ ID NO: 69) | TPGPGIRY | HIV(B35)-14 (SEQ ID NO: 1) | NPDIVIYQY |
| HIV(B35)-4 (SEQ ID NO: 70) | PPIPVGEIY | HIV(B35)-15 (SEQ ID NO: 87) | EPPFLWMGY |
| HIV(B35)-5 (SEQ ID NO: 71) | GPKEPFRDY | HIV(B35)-16 (SEQ ID NO: 3) | TPPLVKLWY |
| HIV(B35)-6 (SEQ ID NO: 72) | QPKTACTTCY | HIV(B35)-18 (SEQ ID NO: 4) | EPIVGAETFY |
| HIV(B35)-7 (SEQ ID NO: 73) | NPPIPVGEIY | HIV(B35)-19 (SEQ ID NO: 88) | EPFKNLKTGKY |
| HIV(B35)-8 (SEQ ID NO: 74) | EPFRDYVDRFY | HIV(B35)-20 (SEQ ID NO: 89) | IPAETGQETAY |
| HIV(B35)-10 (SEQ ID NO: 75) | TPGIRYQY | | |
| HIV(B35)GAG-8 (SEQ ID NO: 76) | TPQDLNTML | HIV(B35)GAG-21 (SEQ ID NO: 90) | GPGHKARVL |
| HIV(B35)GAG-13 (SEQ ID NO: 25) | NPPIPVGEI | HIV(B35)GAG-26 (SEQ ID NO: 91) | APPEESFRF |
| HIV(B35)GAG-20 (SEQ ID NO: 77) | GPAATLEEM | | |
| HIV(B35)POL-1 (SEQ ID NO: 78) | LPGRWKPKM | HIV(B35)POL-20 (SEQ ID NO: 5) | SPAIFQSSM |
| HIV(B35)POL-7 (SEQ ID NO: 27) | VPVKLKPGM | HIV(B35)POL-27 (SEQ ID NO: 92) | YPGIKVRQL |
| HIV(B35)POL-9 (SEQ ID NO: 79) | GPKVKQWPL | | |
| HIV(B35)ARV2-1 (SEQ ID NO: 80) | EPIDKELY | HIV(B35)ARV2-25 (SEQ ID NO: 7) | EPIVGAETF |
| HIV(B35)ARV2-2 (SEQ ID NO: 81) | EPVHEVYY | HIV(B35)ARV2-26 (SEQ ID NO: 93) | QPDKSESEL |
| HIV(B35)ARV2-3 (SEQ ID NO: 82) | QPRTACNNCY | HIV(B35)ARV2-27 (SEQ ID NO: 29) | LPPVVAKEI |
| HIV(B35)ARV2-4 (SEQ ID NO: 8) | VPLDKDFRKY | HIV(B35)ARV2-28 (SEQ ID NO: 94) | VPRRKAKII |
| HIV(B35)ARV2-5 (SEQ ID NO: 83) | RPWLHSLGQY | HIV(B35)ARV2-29 (SEQ ID NO: 95) | DPGLADQLI |
| HIV(B35)ARV2-6 (SEQ ID NO: 9) | RPQVPLRPMTY | HIV(B35)ARV2-30 (SEQ ID NO: 96) | TPKKTKPPL |
| HIV(B35)ARV2-7 (SEQ ID NO: 84) | RPNNNTRKSIY | HIV(B35)ARV2-31 (SEQ ID NO: 97) | PPLPSVKKL |
| HIV(B35)ARV2-8 (SEQ ID NO: 2) | PPVRPQVLP | HIV(B35)ARV2-32 (SEQ ID NO: 30) | PPRPWLHSL |
| HIV(B35)ARV2-9 (SEQ ID NO: 98) | RPQVPLRPM | HIV(B35)ARV2-33 (SEQ ID NO: 11) | DPNPQEVVL |
| HIV(B35)ARV2-10 (SEQ ID NO: 99) | RRPMTYKAAL | HIV(B35)ARV2-34 (SEQ ID NO: 103) | KPCVKLTPL |
| HIV(B35)ARV2-11 (SEQ ID NO: 6) | YPLTFGWCF | HIV(B35)ARV2-35 (SEQ ID NO: 31) | CPKVSFEPI |
| HIV(B35)ARV2-12 (SEQ ID NO: 100) | LPPLERLTL | HIV(B35)ARV2-36 (SEQ ID NO: 12) | RPIVSTQLL |
| HIV(B35)ARV2-18 (SEQ ID NO: 101) | TPSQKQEPI | HIV(B35)ARV2-37 (SEQ ID NO: 104) | DPEIVMHSF |
| HIV(B35)ARV2-19 (SEQ ID NO: 28) | YPLTSLRSL | HIV(B35)ARV2-38 (SEQ ID NO: 13) | LPCRIKQII |

TABLE 1-continued

| | | | |
|---|---|---|---|
| HIV(B35)ARV2-20 (SEQ ID NO: 102) | LPGKWKPKM | HIV(B35)ARV2-39 (SEQ ID NO: 105) | SPLSFQTRL |
| HIV(B35)ARV2-24 (SEQ ID NO: 10) | IPLTEEAEL | | |

(2) Determination of Ability of Synthetic HIV Peptides to Bind to HLA-B * 3501 Antigen:

Using a mouse cell line of RMA-S strain which express HLA-B * 3501, the synthesized HIV peptides were examined as to whether, or not, they could bind to the HLA-B * 3501 antigen.

2-1. Preparation of RMA-S-B * 3501 Cells:

HLA-B * 3501 gene may be cloned starting from a chromosomal DNA of human peripheral blood lymphocytes carrying the HLA-B * 3501 antigen according to a method previously reported (Ooba et al., Immunogenetics, 1989, 30, p. 76). More specifically, the chromosomal DNA was prepared from human peripheral blood lymphocytes carrying the HLA-B * 3501 antigen, according to an ordinary method, followed by digesting the DNA with a restriction enzyme EcoRI and subjecting to sucrose density-gradient centrifugation to thus give DNA fragments of 6.0 to 8.5 kb. These DNA fragments were inserted into a phage vector δ ZAP (purchased from Toyobo Co., Ltd.) to give a genomic library. This library was screened using HLA-B7 cDNA (Coppin et al., Proc. Natl. Acad. Sci. USA, 1985, 82, p. 8614) as a probe to obtain a clone carrying the HLA-B * 3501 gene. The resulting gene was incorporated into RMA-S cells (Ljunggren at al., J. Immunol., 1989, 142, p. 2911) for introgression according to electroporation and the cell capable of expressing the gene was selected by flow cytometry using an anti-HLA-Bw6 monoclonal antibody, SFR8·B6 (ATCC HB152). The RMA-S-B* 3501 cell is deposited, under the Budapest Treaty, with the National Institute of Bioscience and Human-Technology, Agency of Industrial Science and Technology, under the accession number of FERM BP-4727.

2-2. Determination of Ability of HIV Synthetic Peptide to Bind to HLA-B* 3501 Antigen, Using RMA-S-B * 3501 Cells:

The RMA-S cell is a mouse cell line which is deficient in TAP (transporter associated protein) antigen. Therefore, when cultivated at 37° C., the cell expresses an MHC class I antigen on their surface only at a low level. However, it has been known that, when cultivated at a low temperature (26° C.), the cell expresses a class I antigen free of any peptide incorporated therein, on the surface at a high level (Ljunggren et al., Nature, 1990, 346, p. 476).

RMA-S-B * 3501 cells likewise express the HLA-B * 3501 antigen on the surface at a high level, when cultivated at 26° C., but the degree of the antigen-expression is lowered when they are cultivated at 37° C. Moreover, The degree of the HLA-B * 3501 antigen expression on the RMA-S-B * 3501 cells that have been cultivated at 26° C. is lowered to the same degree observed when the cells are cultivated at 37° C., if the cells are allowed to stand at 37° C. for 3 hours. However, when a foreign peptide binds to the HLA-B * 3501 antigen free of any peptide bound thereto, the peptide-bound HLA-B * 3501 antigen does not disappear even though the cells are allowed to stand at 37° C. and thus the cells maintain a high ability of expressing the antigen. FIG. 1 shows the variation in the expression level of HLA-B* 3501 observed when adding autoantigenic peptide 28H (LPGPKFLQY (SEQ ID NO: 113): represented by Δ in the graph), 37 F (LPFDFTPGY (SEQ ID NO: 114): represented by ○ in the graph) capable of binding to an HLA-B * 3501 antigen or a peptide MP-1 free of any ability of binding to the same antigen (KGILGKVFTLTV (SEQ ID NO: 115): represented by □ in the graph). These results indicate that the quantity of the HLA-B * 3501 antigen-expression depends on the added amount of the peptide having an ability to bind thereto. The autoantigenic peptides 28H and 37F having an ability to bind to the HLA-B * 3501 antigen and the peptide MP-1 free of such an ability are described in Nature, 1992, 360, p. 434 and Immunogenetics, 1993, 38, p. 161. Accordingly, the binding activity of foreign peptides to HLA-B * 3501 has never been able to be easily determined and evaluated, while using the amount of the HLA-B * 3501 antigen expressed on the cell surface as an indication, until this experimental system is used. The binding activity of a peptide to be examined was actually determined by adding the peptide to the RMA-S-B * 3501 cells cultivated at 26° C., followed by allowing the mixture to stand at 26° C. for one hour and then at 37° C. for 3 hours and thereafter determining the HLA-B * 3501 antigen-expression level by flow cytometry using an anti-HLA-Bw6 monoclonal antibody and SFR8·B6. In FIG. 1, ▲ indicates a peptide-free control, ● a control in which the cultivation was carried out only at 26° C. in the absence of any peptide, and ■ a control in which the cultivation was carried out only at 37° C. in the absence of any peptide.

Fifty-eight kinds of HIV peptides were inspected for the ability thereof to bind to the HLA-B * 3501 antigen and it was found that 26 peptides out of these peptides could bind to the antigen, as shown in Table 2.

TABLE 2

| Binding Affinity | Peptide | Sequence | Position |
|---|---|---|---|
| High Affinity | HIV(B35)-3 (SEQ ID NO. 69) | TPGPGIRY | nef 133–139 |
| | HIV(B35)-14 (SEQ ID NO. 1) | NPDIVTYQY | pol 330–338 |
| | HIV(B35)ARV2-8 (SEQ ID NO. 2) | FPVRPQVPL | nef 72–80 |
| Middle Affinity | HIV(B35)-16 (SEQ ID NO: 3) | TPPLVKLWY | pol 574–582 |
| | HIV(B35)-18 (SEQ ID NO: 4) | EPIVGAETFY | pol 587–596 |
| | HIV(B35)-20 (SEQ ID NO: 89) | IPAETGQETAY | pol 804–814 |
| | HIV(B35)POL-20 (SEQ ID NO: 5) | SPAIFQSSM | pol 311–319 |
| | HIV(B35)ARV2-11 (SEQ ID NO: 6) | YPLTFGWCF | nef 139–147 |
| | HIV(B35)ARV2-19 (SEQ ID NO: 28) | YPLTSLRSL | gag 486–494 |
| | HIV(B35)ARV2-25 (SEQ ID NO: 7) | EPIVGAETF | pol 587–595 |
| Low | HIV(B35)-7 (SEQ ID NO: 73) | NPPIPVGEIY | gag 255–264 |

TABLE 2-continued

| Binding Affinity | Peptide | Sequence | Position |
|---|---|---|---|
| Affinity | HIV(B35)-8 (SEQ ID NO: 74) | EPFRDYVDRFY | gag 293–303 |
| | HIV(B35)-15 (SEQ ID NO: 87) | EPPFLWMGY | pol 379–387 |
| | HIV(B35)-19 (SEQ ID NO: 88) | EPFKNLKTGKY | pol 587–596 |
| | HIV(B35)GAG-20 (SEQ ID NO: 77) | GPAATLEEM | gag 340–348 |
| | HIV(B35)GAG-26 (SEQ ID NO: 91) | APPEESFRF | gag 459–467 |
| | HIV(B35)ARV2-1 (SEQ ID NO: 80) | EPIDKELY | gag 479–486 |
| | HIV(B35)ARV2-2 (SEQ ID NO: 81) | EPVHEVYY | pol 467–474 |
| | HIV(B35)ARV2-4 (SEQ ID NO: 8) | VPLDKDFRKY | pol 273–282 |
| | HIV(B35)ARV2-6 (SEQ ID NO: 9) | RPQVPLRPMTY | nef 75–85 |
| | HIV(B35)ARV2-9 (SEQ ID NO: 98) | RPQVPLRPM | nef 75–83 |
| | HIV(B35)ARV2-12 (SEQ ID NO: 100) | LPPLERLTL | rev 75–83 |
| | HIV(B35)ARV2-24 (SEQ ID NO: 10) | IPLTEEAEL | pol 448–456 |
| | HIV(B35)ARV2-33 (SEQ ID NO: 11) | DPNPQEVVL | env 77–85 |
| | HIV(B35)ARV2-36 (SEQ ID NO: 12) | RPIVSTQLL | env 255–263 |
| | HIV(B35)ARV2-38 (SEQ ID NO: 13) | LPCRIKQII | env 413–421 |

(3) Induction of CTL in HIV-Infected Patients Using Peptides Having Ability to Bind to HLA-B * 3501:

Lymphocytes were isolated from three HIV-infected patients carrying HLA-B * 3501, i.e., Patient A (HLA-A24/31, B35/61, Cw3/–), Patient B (HLA-A24/26, B35/61, Cw3/–) and Patient C (HLA-A24/26, B35/51, Cw3/–). These lymphocytes were isolated according to the usual Ficoll-Conray gravity centrifugation (Junichi YATA & Michio FUJIWARA, "Shin-Rinpakyu Kino Kensakuho (Novel Method of Searching for Functions of Lymphocytes)", published by Chugai Igaku Co., Ltd., 1987); Shin-Seikagaku Jikken Koza (New Lectures on Biochemical Experiments) No. 12: "Bunshi Menekigaku (Molecular Immunology) I", published by Tokyo Kagaku Dojin K.K., 1989). More specifically, the blood was collected from each patient, using a heparin-containing syringe, followed by diluting it with physiological saline, applying the diluted blood sample onto a Ficoll-Paque separation solution (available from Pharmacia Company) and then centrifugation (400× g) for 30 minutes at room temperature. The lymphocytes-containing fraction as the middle layer of the supernatant was recovered using a pipette, washed and then used in the following procedures. The resulting fraction was dispensed into wells of a 24-well cultivation plate such that the lymphocytes were distributed at a density of $2\times10^6$ cells/well and then cultured in RPMI 1640 culture medium (containing 10% FCS) to which human recombinant IL-2 and a synthetic peptide were supplemented to a final concentration of 50 U/ml and 1 μM, respectively. A half of the culture medium was replaced with RPMI 1640 culture medium containing 50 U/ml of IL-2, at intervals of 2 to 3 days. After one week, autologous lymphocytes ($1\times10^6$) that had been stimulated with PHA and then irradiated with radioactive rays and 1 μM of the synthetic peptide were added to each well to thus again stimulate and proliferate specific CTL cells in each well. Thereafter, the cultivation was continued for additional one week to determine the CTL activity in each well.

(4) Determination of Cytotoxic Activity of CTL Induced by Peptides Capable of Binding to HLA-B * 3501:

4-1. Preparation of T2-B * 3501 Cells:

HLA-B * 3501 gene was introduced into TAP antigenic gene-deficient human lymphocytic cell line, T2 cells (Salter et al., EMBO J., 1986, 5, p. 943) for introgression by electroporation, and the gene-expressing cells were screened by flow cytometry using a monoclonal antibody SFR * B6. The cell is named T2-B * 3501 cell. The T2-B * 3501 cell is deposited, under the Budapest Treaty, with the National Institute of Bioscience and Human-Technology, Agency of Industrial Science and Technology under the accession number of FERM BP-4726.

When patients carrying HLA-B35 are infected and attacked with HIV, the HIV-infected lymphocytes thereof express an HLA-B * 3501 antigen on the surface thereof to thus present HIV peptides. The T2-B * 3501 cells express a large amount of an HLA-B * 3501 antigen free of any peptide bound thereto, when cultivated at 26° C., like the RMA-S-B * 3501 cells discussed in Section (2). Accordingly, peptides were bound to the cells under such conditions to thus artificially establish desired HIV-infected lymphocytes which were used as target cells for the determination of the cytotoxic activity of CTL.

4-2. Determination of Cytotoxic Activity of CTL:

The T2-B * 3501 cells or T2 cells ($1\times10^6$) were treated with 100 μCi of $Na_2{}^{51}CrO_4$ for 90 minutes at 26° C. and then washed three times with 10% FCS-containing RPMI 1640 culture medium to prepare labeled target cells. To each well of a 96-well plate, there were added the labeled target cells ($5\times10^3$ cells; T2 or T2-B * 3501 cells) suspended in 50 μl of the culture medium. Moreover, 5 μl of a synthetic peptide solution which was variously diluted to a concentration ranging from $4\times10^{-4}$ μM to 4 μM was added to the wells. These wells were then allowed to stand in a $CO_2$ incubator for 30 minutes. Afterwards, the patient's peripheral blood lymphocytes that had been stimulated with the foregoing peptides obtained in Section (3) were added to each well in a number of $1\times10^5$, $2.5\times10^4$ or $6.25\times10^3$ cells to thus suspend the cells in 100 μl of the culture medium. The plate was allowed to stand in a $CO_2$ incubator maintained at 37° C. for 4 hours. Thereafter, a half of the culture medium (100 μl) was taken out from each well, and the amount of $^{51}Cr$ released from the target cells due to the cytotoxic activity of the cultivated patient's peripheral blood lymphocytes was determined using a gamma counter. The specific cytotoxic activity is calculated according to the following equation:

Specific Cytotoxic Activity=[(measured value in each cell−minimum released amount)/(maximum released amount−minimum released amount)]×100 wherein the minimum released amount represents the measured value for the well containing only the target cells, which means the amount of $^{51}Cr$ spontaneously released from the target cells; and the maximum released amount represents the label-released value observed when the target cells were destructed by the addition of a surfactant Triton X-100 thereto.

Figure 2:
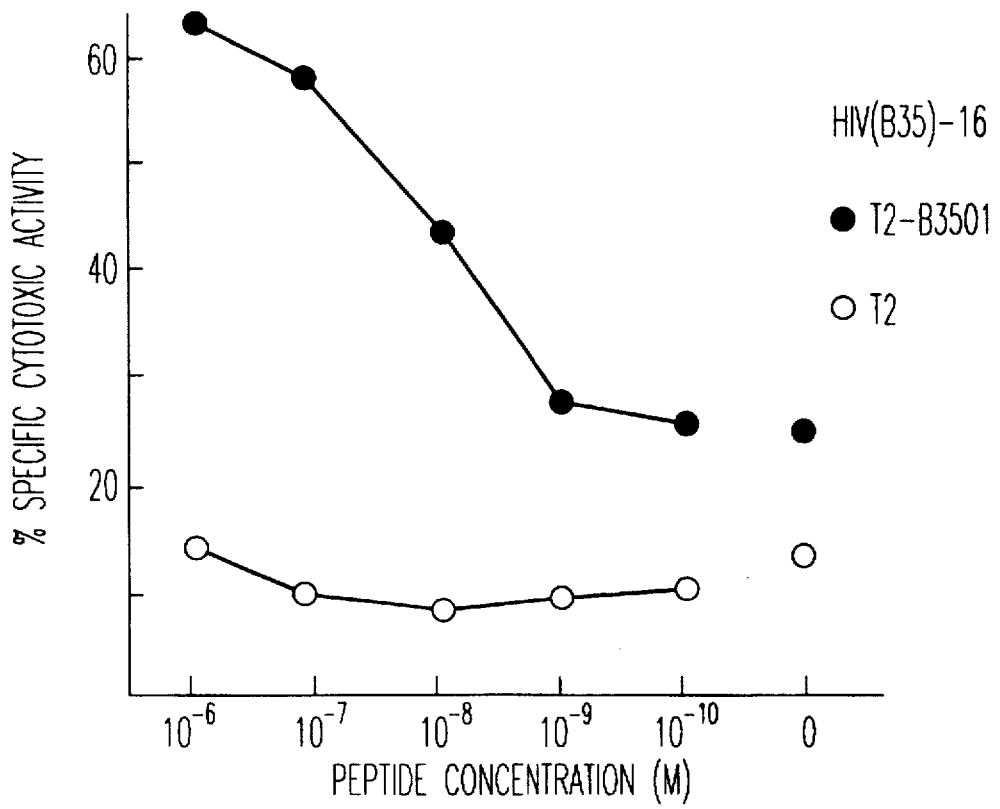
FIG. 2 shows the specific cytotoxic activity of CTL induced by a peptide HIV(B35)-16 (SEQ ID NO: 3), in which ● represents the activity observed when T2-B * 3501 cells are used as the target cells and ○ represents the activity observed when T2 cells are used as the target cells, the latter serving as a control. In this experiment, used were $1 \times 10^5$, $2.5 \times 10^4$ or $6.25 \times 10^3$ patient's peripheral lymphocytes that had been stimulated with the peptide and cultivated. The data of the specific cytotoxic activity against the target cells shown in FIG. 2 are those obtained when using $1 \times 10^5$ lymphocytes.
Figure 3:
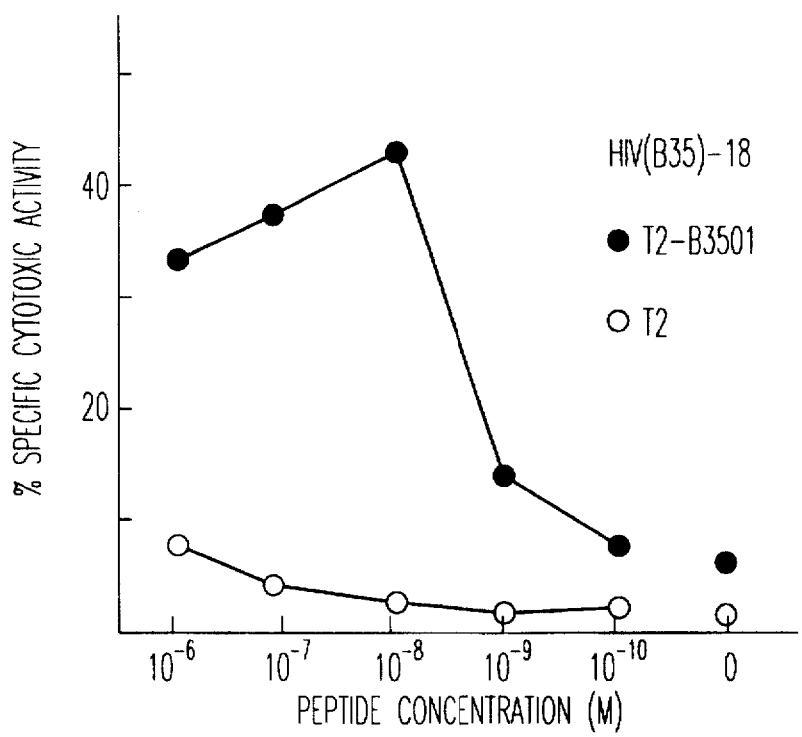
FIG. 3 shows the specific cytotoxic activity of CTL induced by a peptide HIV(B35)-18 (SEQ ID NO: 4), in which ● represents the activity observed when T2-B * 3501 cells are used as the target cells and ○ represents the activity observed when T2 cells are used as the target cells, the latter serving as a control. In this experiment, used were $1 \times 10^5$, $2.5 \times 10^4$ or $6.25 \times 10^3$ patient's peripheral lymphocytes that had been stimulated with the peptide and cultivated. The data of the specific cytotoxic activity against the target cells shown in FIG. 3 are those obtained when using $1 \times 10^5$ lymphocytes.
Figure 4:
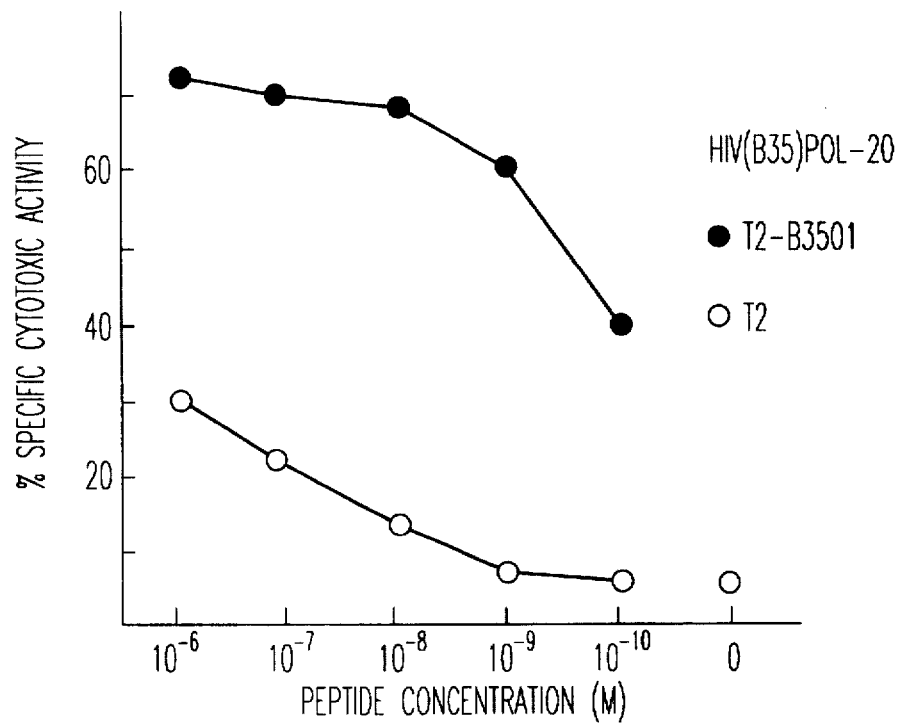
FIG. 4 shows the specific cytotoxic activity of CTL induced by a peptide HIV(B35)POL-20 (SEQ ID NO: 5), in which ● represents the activity observed when T2-B * 3501 cells are used as the target cells and ○ represents the activity observed when T2 cells are used as the target cells, the latter serving as a control. In this experiment, used were $1 \times 10^5$, $2.5 \times 10^4$ or $6.25 \times 10^3$ patient's peripheral lymphocytes that had been stimulated with the peptide and cultivated. The data of the specific cytotoxic activity against the target cells shown in FIG. 4 are those obtained when using $1 \times 10^5$ lymphocytes.

The results are plotted on FIGS. 2, 3 and 4. FIG. 2 shows the results observed for HIV(B35)-16 (Sequence Number 3);

FIG. 3 the results observed for HIV(B35)-18 (Sequence Number 4); and FIG. 4 the results observed for HIV(B35) POL-20 (Sequence Number 6). These results clearly indicate that these synthetic peptides were effective for inducing CTLs capable of damaging the synthetic peptide-binding T2-B * 3501 cells.

The peptides listed in Table 2 were examined as to whether they could induce immune responses to HIV according to the same method discussed above. Among these, those capable of inducing immune responses to HIV are summarized in Table 3.

TABLE 3

| Binding Affinity | Peptide | Sequence | Position |
| --- | --- | --- | --- |
| High Affinity | HIV(B35)-14 (SEQ ID NO. 1) | NPDIVIYQY | pol 330–338 |
| | HIV(B35)ARV2-8 (SEQ ID NO. 2) | FPVRPQVPL | nef 72–80 |
| Middle Affinity | HIV(B35)-16 (SEQ ID NO: 3) | TPPLVKLWY | pol 574–582 |
| | HIV(B35)-18 (SEQ ID NO: 4) | EPIVGAEIFY | pol 587–596 |
| | HIV(B35)POL-20 (SEQ ID NO: 5) | SPAIFQSSM | pol 311–319 |
| | HIV(B35)ARV2-11 (SEQ ID NO: 6) | YPLTFGWCF | nef 139–147 |
| | HIV(B35)ARV2-25 (SEQ ID NO: 7) | EPIVGAETF | pol 587–595 |
| Low Affinity | HIV(B35)ARV2-4 (SEQ ID NO: 8) | VPLDKDFRKY | pol 273–282 |
| | HIV(B35)ARV2-6 (SEQ ID NO: 9) | RPQVPLRPMTY | nef 75–85 |
| | HIV(B35)ARV2-24 (SEQ ID NO: 10) | IPLTEEAEL | pol 448–456 |
| | HIV(B35)ARV2-33 (SEQ ID NO: 11) | DPNPQEVVL | env 77–85 |
| | HIV(B35)ARV2-36 (SEQ ID NO: 12) | RPIVSTQLL | env 255–263 |
| | HIV(B35)ARV2-38 (SEQ ID NO: 13) | LPCRIKQII | env 413–421 |

In the same manner used above, HIV sequences of MN strain, NDK strain and HXB2 strain were tested. As a result, the peptides shown in Table 4 were selected.

TABLE 4

| Binding Affinity | Peptide | Sequence | Position |
| --- | --- | --- | --- |
| High Affinity | HIV(B35)GAG-24 (SEQ ID NO: 14) | FPQSRIEPT | gag 450–458 (MN) |
| | HIV(B35)POL-5 (SEQ ID NO: 15) | FPISPIETV | pol 155–163 |
| Middle Affinity | HIV(B35)-17 (SEQ ID NO: 16) | VPLDEDFRKY | pol 182–191 (HXB2) |
| | HIV(B35)-29 (SEQ ID NO: 17) | EPIIGAETFY | pol 586–595 (NDK) |
| | HIV(B35)GAG-9 (SEQ ID NO: 18) | HPVHAGPIT | gag 219–227 (MN) |
| | HIV(B35)GAG-29 (SEQ ID NO: 19) | YPLASLKSL | gag 490–498 (MN) |
| Low Affinity | HIV(B35)-9 (SEQ ID NO: 20) | KPQVPLRPMTY | nef 73–83 (MN) |
| | HIV(B35)-12 (SEQ ID NO: 21) | EPVHGVYY | pol 466–473 (NDK) |
| | HIV(B35)-25 (SEQ ID NO: 22) | NPEIVIYQY | pol 329–327 (NDK) |
| | HIV(B35)GAG-4 (SEQ ID NO: 23) | VPIVQNIEG | gag 135–143 (MN) |
| | HIV(B35)POL-26 (SEQ ID NO: 24) | LPEKDSWTV | pol 401–409 |

EXAMPLE 2

The same procedures used in Example 1 were repeated except that there was used, as the HLA-binding motif, a motif of an HLA-B51-binding antigenic peptide which had a sequence consisting of 8 to 11 amino acid residues, whose second residue was an amino acid residue selected from the group consisting of Pro, Ala and Gly and whose C-terminal was an amino acid residue selected from the group consisting of Ile, Leu, Val, Phe and Met and that a protein sequence of HIV SF-2 strain and RMA-S-B * 5101 cells were used to give peptides capable of inducing immune responses to HIV. These peptides are summarized in Table 5. In this connection, the RMA-S-B * 5101 cell is deposited, under Budapest Treaty, with the National Institute of Bioscience and Human-Technology, Agency of Industrial Science and Technology under the accession number of FERM BP-4834.

TABLE 5

| Peptide | Sequence | Position |
| --- | --- | --- |
| HIV-B35-GAG-13(A55) (SEQ ID NO:25) | NPPIPVGEI | GAG255–264 |
| HIV-B35-GAG-29(A69) (SEQ ID NO:26) | YPLASLKSL | GAG490–498 |
| HIV-B35-POL-5(A74) (SEQ ID NO:15) | FPISPIETV | POL155–163 |
| HIV-B35-POL-7(A76) (SEQ ID NO:27) | VPVKLKPGM | POL163–171 |
| HIV-B35-POL-26(A95) (SEQ ID NO:24) | LPEKDSWTV | POL401–409 |
| HIV-B35-SF2-8(C-1) (SEQ ID NO:2) | FPVRPQVPL | NEF71–80 |
| HIV-B35-SF2-21(C-7) (SEQ ID NO:28) | YPLTSLRSL | GAG486–494 |
| HIV-B35-SF2-27(C-12) (SEQ ID NO:29) | LPPVVAKEI | POL743–751 |
| HIV-B35-SF2-32(C-17) | FPRPWLHSL | VPR34–42 |

TABLE 5-continued

| Peptide | Sequence | Position |
|---|---|---|
| (SEQ ID NO:30) HIV-B35-SF2-35(C-20) | CPKVSFEPI | ENV208–216 |
| (SEQ ID NO:31) HIV-B35-SF2-38(C-23) | LPCRIKQII | ENV413–421 |
| (SEQ ID NO:13) HIV-B35-33(C-31) | YPCTVNFTI | ENV618–626 |
| (SEQ ID NO:106) HIV-B35-34(C-32) | LPALSTGLI | ENV682–690 |
| (SEQ ID NO:107) HIV-B35-36(C-34) | CPSGHAVGI | ENV1171–1179 |
| (SEQ ID NO:108) HIV-B35-39(C-37) | IPTSGDVVI | ENV1426–1434 |
| (SEQ ID NO:109) HIV-B35-50(C-48) | LPPTIGPPI | ENV2316–2324 |
| (SEQ ID NO:110) HIV-B35-55(C-53) | APTLWARMI | ENV2835–2843 |
| (SEQ ID NO:111) HIV-B35-56(C-54) | EPLDLPQII | ENV2874–2882 |
| (SEQ ID NO:112) HIV-B51-3(H-3) | NANPDCKTI | GAG327–335 |
| (SEQ ID NO:32) HIV-B51-7(H-7) | TAVQMAVFI | POL989–997 |
| (SEQ ID NO:33) HIV-B51-9(H-9) | RAFHTTGRI | ENV316–324 |
| (SEQ ID NO:34) HIV-B51-10(H-10) | YAPPIGGQI | ENV432–440 |
| (SEQ ID NO:35) HIV-B51-11(H-11) | QARQLLSGI | ENV539–547 |
| (SEQ ID NO:36) HIV-B51-12(H-12) | VAQRAYRAI | ENV831–839 |
| (SEQ ID NO:37) HIV-B51-13(H-13) | RAYRAILHI | ENV834–842 |
| (SEQ ID NO:38) HIV-B51-29(H-18) | VGPTPVNII | POL133–141 |
| (SEQ ID NO:39) HIV-B51-32(H-21) | QGWKGSPAI | POL306–314 |
| (SEQ ID NO:40) HIV-B51-43(H-32) | VGGLVGLRI | ENV688–696 |
| (SEQ ID NO:41) HIV-B51-53(H-42) | DARAYDTEV | ENV56–64 |
| (SEQ ID NO:42) HIV-B51-54(H-43) | NALFRNLDV | ENV171–179 |
| (SEQ ID NO:43) HIV-B51-70(H-50) | IPLGDAKLV | VIF57–65 |
| (SEQ ID NO:44) HIV-B51-71(H-51) | GPCTNVSTV | ENV240–248 |
| (SEQ ID NO:45) HIV-B51-83(H-63) | CGHKAIGTV | POL123–131 |
| (SEQ ID NO:46) | | |

EXAMPLE 3

The same procedures used in Example 1 were repeated except that there was used, as the HLA-binding motif, a motif of an HLA-A * 3101-binding antigenic peptide which had a sequence consisting of 8 to 11 amino acid residues, whose second residue was an amino acid residue selected from the group consisting of Leu, Val, Tyr and Phe and whose C-terminal was an amino acid residue Arg and that a protein sequence of HIV MN strain or HIV SF-2 strain and RMA-S-A * 3101 cells were used to give peptides capable of inducing immune responses to HIV. These peptides are summarized in Table 6. In this connection, the RMA-S-A * 3101 cell is deposited, under Budapest Treaty, with the National Institute of Bioscience and Human-Technology, Agency of Industrial Science and Technology under the accession number of FERM BP-4833.

TABLE 6

| Peptide | Sequence | Position | $K^d$ Value |
|---|---|---|---|
| C-119 | IVMHSFNCR (SEQ ID NO:47) | ENV373–381 | $3.0 \times 10^{-5}$ |
| C-121 | VLAVERYLR (SEQ ID NO:48) | ENV579–587 | $9.0 \times 10^{-5}$ |
| C-117 | NYRLIHCNR (SEQ ID NO:49) | ENV193–201 | $1.1 \times 10^{-4}$ |
| C-104 | MVHQAISPR (SEQ ID NO:50) | GAG144–152 | $1.4 \times 10^{-4}$ |
| C-114 | SVKKLTEDR (SEQ ID NO:51) | VIF165–173 | $1.4 \times 10^{-4}$ |
| C-124 | SLCLFSYRR (SEQ ID NO:52) | ENV761–769 | $2.2 \times 10^{-4}$ |
| C-125 | CLFSYRRLR (SEQ ID NO:53) | ENV763–771 | $2.2 \times 10^{-4}$ |
| C-111 | AVFIHNFKR (SEQ ID NO:54) | POL893–901 | $2.9 \times 10^{-4}$ |
| C-100 | KLAFHHMAR (SEQ ID NO:55) | NEF192–200 | $3.7 \times 10^{-4}$ |
| C-118 | TVQCTHGIR (SEQ ID NO:56) | ENV247–255 | $7.4 \times 10^{-4}$ |
| C-113 | ILGYRVSPR (SEQ ID NO:57) | VIF124–132 | $8.9 \times 10^{-4}$ |
| C-112 | IVWQVDRMR (SEQ ID NO:58) | VIF9–17 | $>10^{-4}$ |
| C-98 | PVRPQVPLR (SEQ ID NO:59) | NEF73–81 | $>10^{-4}$ |
| C-126 | ILHIHRRIR (SEQ ID NO:60) | ENV838–846 | $>10^{-4}$ |
| C-106 | ELYPLTSLR (SEQ ID NO:61) | GAG424–432 | $>10^{-4}$ |
| C-123 | VLSIVNRVR (SEQ ID NO:62) | ENV700–708 | $>10^{-4}$ |
| C-122 | IVGGLVGLR (SEQ ID NO:63) | ENV687–695 | $>10^{-4}$ |

Industrial Applicability

The peptides of the present invention can induce immune responses to HIV and therefore, can effectively be used as anti-AIDS agents for preventing and curing AIDS. More specifically, they can be used in anti-AIDS vaccines comprising the foregoing peptides and in anti-AIDS vaccines comprising vaccinia viruses and BCG bacteria carrying recombinant DNA's containing DNA's coding for the foregoing peptides. Moreover, the cytotoxic T cells obtained by cultivating peripheral blood lymphocytes carrying HLA-B antigens in the presence of the foregoing peptides can be used as anti-AIDS agents for treating patients suffering from AIDS.

We claim:

1. A peptide fragment of an HIV protein which
   has a length of 8 to 11 amino acid residues,
   binds to HLA, and
   induces production of cytotoxic T lymphocytes against cells infected with HIV,
   wherein
   the second amino acid residue is Pro, and
   the C-terminal amino acid residue is selected from the group consisting of Tyr, Leu, Ile, Met, Phe and Ala.

2. The peptide fragment of claim 18, wherein the HIV protein is selected from the group consisting of pol, gag, vpr, vif, rev and env.

3. The peptide fragment of claim 1 having the sequence of SEQ ID NO: 1, 2, 3, 4, 5, 6, 7, 8, 9, 10, 11, 12, 13, 14, 15, 16, 17, 18, 19, 20, 21, 22, 23 or 24.

4. A peptide fragment of an HIV protein which
   has a length of 8 to 11 amino acid residues,
   binds to HLA, and
   induces production of cytotoxic T lymphocytes against cells infected with HIV, wherein
   the second amino acid residue is selected from the group consisting of Pro, Ala and Gly, and
   the C-terminal amino acid residue is selected from the group consisting of Ile, Leu, Val, Phe and Met.

5. The peptide fragment of claim 4, wherein the HIV protein is selected from the group consisting of pol, gag, vpr, vif, rev and env.

6. The peptide fragment of claim 3 having the sequence of SEQ ID NO: 25, 26, 27, 28, 29, 30, 31, 32, 33, 34, 35, 36, 37, 38, 39, 40, 41, 42, 43, 44, 45 or 46.

7. A peptide fragment of an HIV protein which
   has a length of 8 to 11 amino acid residues,
   binds to HLA, and
   induces production of cytotoxic T lymphocytes against cells infected with HIV, wherein
   the second amino acid residue is selected from the group consisting of Leu, Val, Tyr, and Phe, and
   the C-terminal amino acid residue is Arg.

8. The peptide fragment of claim 7, wherein the HIV protein is selected from the group consisting of pol, gag, vpr, vif, rev and env.

9. The peptide fragment of claim 5 having the sequence of SEQ ID NO: 47, 48, 49, 50, 51, 52, 53, 54, 55, 56, 57, 58, 59, 60, 61, 62 or 63.

10. An immunogenic composition, comprising the peptide fragment of claim 1 and a pharmaceutically acceptable carrier and/or a pharmaceutically acceptable diluent.

11. An immunogenic composition, comprising the peptide fragment of claim 4 and a pharmaceutically acceptable carrier and/or a pharmaceutically acceptable diluent.

12. An immunogenic composition, comprising the peptide fragment of claim 7 and a pharmaceutically acceptable carrier and/or a pharmaceutically acceptable diluent.

13. A method of inducing cytotoxic T lymphocytes comprising contacting the peptide fragment of claim 1 with peripheral blood lymphocytes having HLA-B antigens.

14. A method of inducing cytotoxic T lymphocytes comprising contacting the peptide fragment of claim 4 with peripheral blood lymphocytes having HLA-B antigens.

15. A method of inducing cytotoxic T lymphocytes comprising contacting the peptide fragment of claim 7 with peripheral blood lymphocytes having HLA-A antigens.

16. A method of inducing cytotoxic T lymphocytes, comprising administering the peptide fragment of claim 1 to a patient in need thereof.

17. A method of inducing cytotoxic T lymphocytes, comprising administering the peptide fragment of claim 4 to a patient in need thereof.

18. A method of inducing cytotoxic T lymphocytes, comprising administering the peptide fragment of claim 7 to a patient in need thereof.

19. A DNA encoding the peptide fragment of claim 1.
20. A DNA encoding the peptide fragment of claim 4.
21. A DNA encoding the peptide fragment of claim 7.

22. A method of screening peptides for induction of cytotoxic T lymphocytes comprising:
    contacting peptide fragments of an HIV protein having a length of 8 to 11 amino acid residues with cells that are deficient in transporter associated protein antigen and express HLA class I antigen;
    selecting peptides which maintain the expression of the HLA class I antigen on the cells; and
    contacting the selected peptides with peripheral blood lymphocytes of a patient infected with HIV.

* * * * *